US012702354B2

(12) United States Patent
Lee et al.

(10) Patent No.: US 12,702,354 B2
(45) Date of Patent: Aug. 11, 2026

(54) BIORHYTHM DETERMINATION METHOD, AND ELECTRONIC DEVICE FOR SUPPORTING SAME

(71) Applicant: Samsung Electronics Co., Ltd., Gyeonggi-do (KR)

(72) Inventors: Younhee Lee, Gyeonggi-do (KR); Hyunsu Kim, Gyeonggi-do (KR); Yumi Park, Gyeonggi-do (KR); Jeongyup Han, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 517 days.

(21) Appl. No.: 17/982,585

(22) Filed: Nov. 8, 2022

(65) Prior Publication Data

US 2023/0061348 A1 Mar. 2, 2023

Related U.S. Application Data

(63) Continuation of application No. PCT/KR2021/000665, filed on Jan. 18, 2021.

(30) Foreign Application Priority Data

May 8, 2020 (KR) ........................ 10-2020-0055324

(51) Int. Cl.
*A61B 5/00* (2006.01)
*A61B 5/11* (2006.01)
*A61B 5/318* (2021.01)

(52) U.S. Cl.
CPC .......... *A61B 5/4857* (2013.01); *A61B 5/4812* (2013.01); *A61B 5/4815* (2013.01);
(Continued)

(58) Field of Classification Search
None
See application file for complete search history.

(56) References Cited

U.S. PATENT DOCUMENTS 10,417,901 B2 9/2019 Park et al.
10,779,802 B2 9/2020 Tholen et al.
(Continued)

FOREIGN PATENT DOCUMENTS

CN 107278139 A 10/2017
JP 2006-94969 A 4/2006
(Continued)

OTHER PUBLICATIONS

Korean Office Action dated Dec. 17, 2024.
(Continued)

*Primary Examiner* — Sana Sahand
(74) *Attorney, Agent, or Firm* — Sughrue Mion, PLLC

(57) ABSTRACT

According to certain embodiments, an electronic device comprises: a sensor module; a processor operatively connected to the sensor module; and a memory operatively connected to the processor, wherein the memory stores instructions that, when executed, cause the processor to perform a plurality of operations comprising: acquiring sensor information through the sensor module, determining sleep information of a user, based on the sensor information, and determining a biorhythm of the user, based on the sleep information.

16 Claims, 12 Drawing Sheets

(52) U.S. Cl.
CPC ............ *A61B 5/742* (2013.01); *A61B 5/7475* (2013.01); *A61B 5/11* (2013.01); *A61B 5/318* (2021.01)

(56) References Cited

U.S. PATENT DOCUMENTS

| | | | | |
|---|---|---|---|---|
| 2016/0015314 | A1* | 1/2016 | Dusanter | A61B 5/4818<br>600/301 |
| 2016/0058428 | A1* | 3/2016 | Shinar | A61B 5/7267<br>600/301 |
| 2020/0000441 | A1 | 1/2020 | Lafon et al. | |

FOREIGN PATENT DOCUMENTS

| | | | |
|---|---|---|---|
| KR | 10-2008-0081737 | A | 9/2008 |
| KR | 10-2015-0083235 | A | 7/2015 |
| KR | 10-2017-0089231 | A | 8/2017 |
| KR | 10-1851690 | B1 | 4/2018 |
| KR | 10-2018-0106781 | A | 10/2018 |
| KR | 10-2018-0138446 | A | 12/2018 |
| KR | 10-2020-0026340 | A | 3/2020 |
| WO | 2013/171799 | A1 | 11/2013 |
| WO | 2016/131630 | A1 | 8/2016 |

OTHER PUBLICATIONS

Korean Office Action dated Aug. 26, 2025.
Communication issued on Jun. 2, 2026 by the Korean Ministry of Intellectual Property in Korean Patent Application No. 10-2020-0055324.

* cited by examiner

BIORHYTHM DETERMINATION METHOD, AND ELECTRONIC DEVICE FOR SUPPORTING SAME

CROSS-REFERENCE TO RELATED APPLICATION(S)

This application is a continuation of International Application No. PCT/KR2021/000665 filed on Jan. 18, 2021, which, in turn claims priority to Korean Patent Application No. KR-10-2020-0055324 filed in the Korean Intellectual Property Office on May 8, 2020.

BACKGROUND

1. Technical Field

Certain embodiments of the present invention relate to technique(s) for determining biorhythm(s).

2. Background Art

Women of childbearing age can undergo a periodic physiological change called a biorhythm (or a menstrual cycle). This biorhythm can be composed of a follicular phase, an ovulatory phase, and a luteal phase according to the characteristics of the physiological change. The biorhythm can include, for example, the follicular phase in which follicles in the ovaries on both sides of the uterus form a cluster and grow to form a mature follicle, the ovulatory phase in which the mature dominant follicle ovulates into the fallopian tube, and the luteal phase of preparing the endometrium so that the fertilized egg can be stably implanted.

This biorhythm is a major indicator considered for anticipation of pregnancy or contraception of women.

A biorhythm can be estimated by adding an average number of days of the biorhythm to a menstrual date. Alternatively, the number of days of the biorhythm may be set by a user. The menstrual date may be directly inputted by the user. Another alternative may be to determine and provide the biorhythm to the user, based on a user's body temperature. However, using a fixed number of days may have limitations in that changes can occur due to psychological factors. Also, using the user's body temperature may be require addition of a temperature sensor.

Certain embodiments of the present disclosure may provide a method of determining a biorhythm based on user's sleep information and an electronic device supporting the same.

SUMMARY

According to certain embodiments, an electronic device comprises: a sensor module; a processor operatively connected to the sensor module; and a memory operatively connected to the processor, wherein the memory stores instructions that, when executed, cause the processor to perform a plurality of operations comprising: acquiring sensor information through the sensor module, determining sleep information of a user, based on the sensor information, and determining a biorhythm of the user, based on the sleep information.

According to certain embodiments, a method comprises: acquiring sensor information through a sensor module in an electronic device; determining sleep information of a user, based on the sensor information; determining a biorhythm of the user, based on the sleep information; and displaying information based on the biorhythm of the user on a display of the electronic device.

BRIEF DESCRIPTION OF THE DRAWINGS

In connection with a description of the drawings, the same or similar reference numerals may be used for the same or similar components.

DETAILED DESCRIPTION

Figure 1:
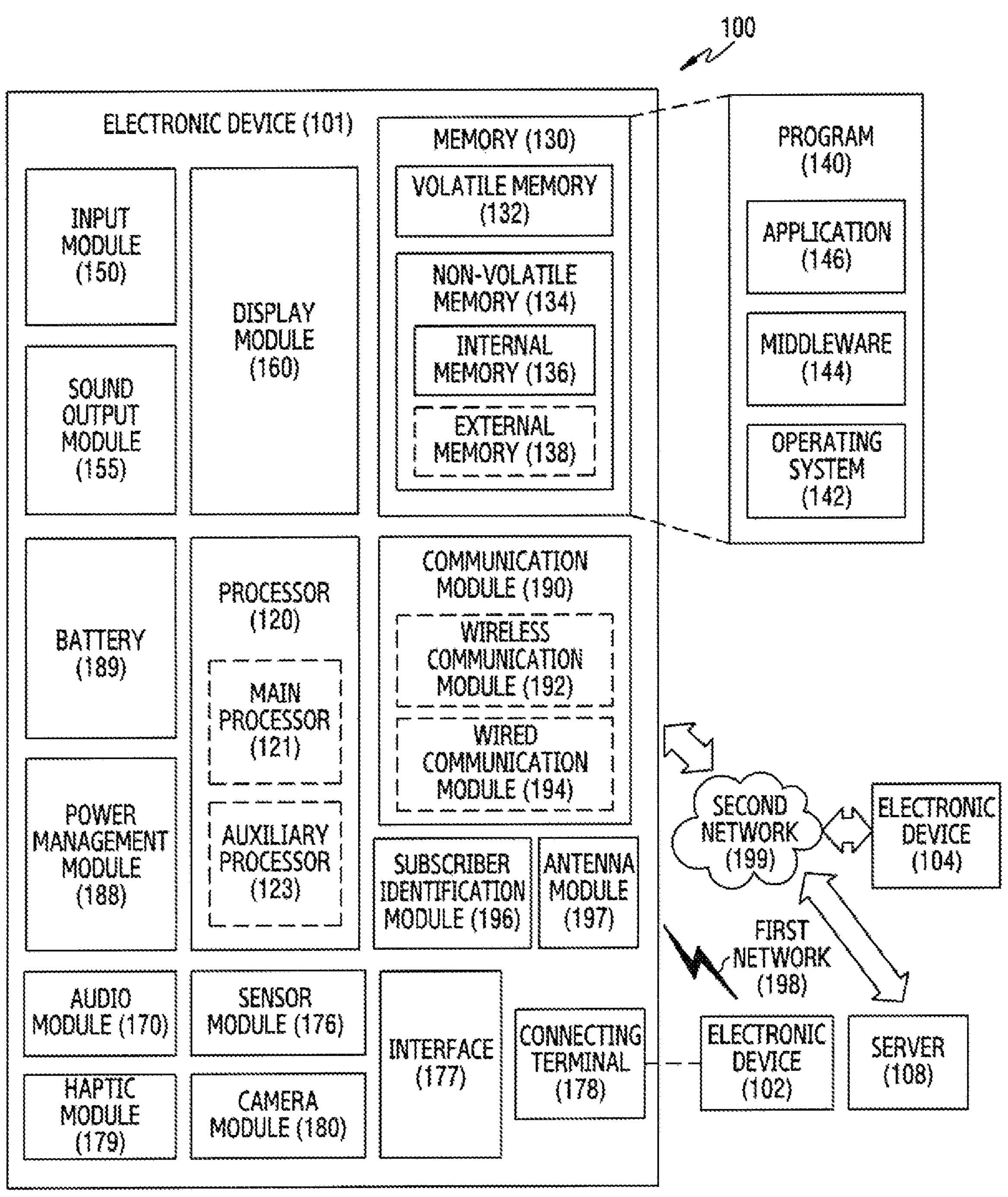
FIG. 1 is a block diagram of an electronic device in a network environment according to certain embodiments.

According to certain embodiments of the present disclosure, an electronic device may use the user's sleep information to more accurately measure the user's actual biorhythm.

Also, according to certain embodiments of the present invention, the biorhythm may be determined without an additional body temperature sensor.

In addition, various effects directly or indirectly identified through the present document may be presented.

Hereinafter, certain embodiments of the present invention will be described with reference to the accompanying drawings. For convenience of description, the size of the components shown in the drawings may be exaggerated or reduced, and the present invention is not necessarily limited as illustrated.

Electronic Device

In FIG. 1, there is described an electronic device 101 that more accurately measure the user's biorhythmic cycles based on the user's sleep information. The electronic device 101 includes a sensor module 176.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). The electronic device 101 may communicate with the electronic device 104 via the server 108. The electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. The processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The term "processor" shall be understood to refer to both the singular and plural contexts in this document.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an image signal processor or a communication processor) may be implemented as part of another component (e.g., the camera module 180 or the communication module 190) functionally related to the auxiliary processor 123. The auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. The receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. The display module 160 may include a touch sensor adapted to detect a touch, or a pressure sensor adapted to measure the intensity of force incurred by the touch.

The audio module 170 may convert a sound into an electrical signal and vice versa. The audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. The interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). The connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. The haptic module 179 may include, for example, a motor, a piezoelectric element, or an electric stimulator.

The camera module 180 may capture a still image or moving images. The camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. The battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). The wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. The antenna module 197 may include an antenna including a radiating element composed of a conductive material or a conductive pattern formed in or on a substrate (e.g., a printed circuit board (PCB)). The antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to certain embodiments, the antenna module 197 may form a mmWave antenna module. The mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101.

According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. The external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
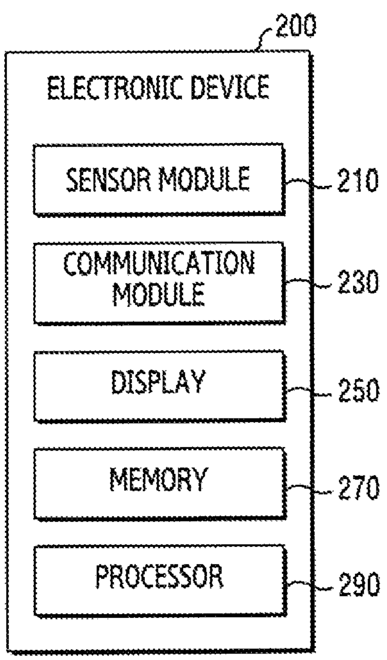
FIG. 2 is a diagram for explaining a construction of an electronic device related to the determination of a biorhythm according to an embodiment of the present invention.

FIG. 2 is a diagram of an electronic device capable of determining a biorhythm according to an embodiment of the present disclosure. The electronic device 200 comprises a sensor module 210, a communication module 230, a display 250, a memory 270, and a processor 290. The memory 270 can store a plurality of executable instructions that are executable by the processor 290, wherein execution of the instructions causes the processor 290 to perform various operation.

The sensor module 210 can transmit an electronic signal, ultrasound, or light to determine the user's sleep activity information. The processor 290 executing the instructions stored in the memory can control the sensor module 210 to acquire the user's sleep activity information and determine the user's biorhythms. The display 250 can output information about the user's biorhythms to the user. The communication module 230 can electronically communicate information about the user's biorhythms.

Referring to FIG. 2, the electronic device 200 (e.g., the electronic device 101 of FIG. 1) may determine a user's biorhythm (e.g., menstrual cycle), based on user's sleep information, and may present the determined biorhythm to a user. To this end, the electronic device 200 may include a sensor module 210 (e.g., the sensor module 176 of FIG. 1), a communication module 230 (e.g., the communication module 190 of FIG. 1), a display 250 (e.g., the display module 160 of FIG. 1), a memory 270 (e.g., the memory 130 of FIG. 1), and a processor 290 (e.g., the processor 120 of FIG. 1). However, the electronic device 200 is not limited thereto. According to certain embodiments, the electronic device 200 may omit at least one of the above-described components, and may further include at least one other component. In an example, the electronic device 200 may omit the communication module 230. In another example, the electronic device 200 may further include a sound output device (e.g., the sound output module 155 of FIG. 1) such as a speaker.

The sensor module 210 may provide an electrical signal or data value corresponding to an external environmental state of the electronic device 200. The sensor module 210 may include, for example, at least one of a motion sensor, a photoplethysmography (PPG) sensor, an electrocardiogram (ECG) sensor, a pressure sensor, an ultrasonic sensor, a sound sensor (microphone), or an illuminance sensor. The sensor module 210 may further include at least one of a temperature sensor and a humidity sensor.

The motion sensor may detect a movement of the electronic device 200. The motion sensor may include, for example, at least one of an acceleration sensor, a gyro sensor, a barometric pressure sensor, and a geomagnetic sensor. The PPG sensor may include a light emitting unit (e.g., a LED) for irradiating light and a light receiving unit (e.g., a photodiode) for detecting the light reflected from a user's skin or transmitted through the skin among the irradiated light. The PPG sensor may convert the light detected through the light receiving unit into an electrical signal and process the converted electrical signal, to measure at least one of a user's heart rate, blood pressure, blood glucose, blood volume, and oxygen saturation. The ECG sensor may include a plurality of electrodes, and process an electrical signal and measure an electrocardiogram of the user. The pressure sensor may measure a pressure applied from the outside. For example, the pressure sensor may detect a pressure applied to a working surface and convert the detected pressure into an electrical signal that may be used for measurement or control. The ultrasonic sensor may emit a sound briefly through a high-frequency sound pulse at regular intervals and, when receiving an echo signal obtained by allowing a sound propagated in the air to collide with an object and reflect, may measure a distance to the object by using a time taken from launch to reception. The microphone may convert a sound into an electrical signal. The illuminance sensor may measure an amount of light coming from the outside, and measure a brightness of the external environment according to the measured amount of light.

The sensor module 210 may detect the user's sleep information. For example, the sensor module 210 may include a motion sensor that senses the degree of motion in the electronic device 200. For example, a period of low motion of the electronic device 200, especially one of approximately 8 hours at night, can be deemed a sleeping period of the user. In another embodiment, the sensor module 210 can include a PPG sensor that measures the user's heartrate or pulse. Based on a period of a lower pulse rate, the electronic device 200 can determine that the user is asleep. In another embodiment, the sensor module 210 can comprise an ECG sensor that measures the user's ECG. Based on the user's ECG, the electronic device 200 can detect a period of time that the user is asleep.

The communication module 230 may support communication between the electronic device 200 and an external electronic device. In an example, the electronic device 200 may transmit and/or receive a command or data with the external electronic device through the communication module 230. In another example, the electronic device 200 may determine a current location, based on a wireless signal received or sensed through the communication module 230.

The display 250 may display various contents (e.g., a text, an image, a video, an icon or a symbol, etc.) to a user. The display 250 may include a touch screen, and may receive, for example, a touch, gesture, proximity, or hovering input that uses an electronic pen or a part of the user's body.

The memory 270 may store various data used by at least one component of the electronic device 200. The memory 270 may store an instruction and data related to the determination of a biorhythm.

The processor 290 may control at least one other component of the electronic device 200, and may perform various data processing or operations. The processor 290 may execute an instruction related to the determination of the biorhythm stored in the memory 270.

The processor 290 may acquire sensor information through the sensor module 210. The processor 290 may acquire sensor information related to a movement of the electronic device 200 through the motion sensor. For example, when a user sleeps in a state in which the user wears the electronic device 200 or brings the electronic device 200 into contact with a part of the user's body, the electronic device 200 may move according to a user's sleep state, and the motion sensor may detect this movement of the electronic device 200. Also, the processor 290, which has acquired the sensor information related to the movement of the electronic device 200 from the motion sensor, may determine the degree of movement and a sleeping posture during a user's sleep through the movement of the electronic device 200.

The processor 290 may acquire sensor information related to at least one of a user's heart rate, blood pressure, blood glucose, blood volume, or oxygen saturation through the PPG sensor. For example, when a user sleeps in a state in which the user wears the electronic device 200 or brings the electronic device 200 into contact with a part of the user's body, the PPG sensor facing the user's skin may irradiate light through the light emitting unit, and detect light reflected from the user's skin or transmitted through the skin through the light receiving unit among the irradiated light and convert the same into an electrical signal, and process the converted electrical signal and measure at least one of a user's heart rate, blood pressure, blood glucose, blood volume or oxygen saturation.

The processor 290 may acquire sensor information related to a user's electrocardiogram through the ECG sensor. For example, when a user sleeps in a state in which the user wears the electronic device 200 or brings the electronic device 200 into contact with a part of the user's body, the processor 290 may measure a potential change dependent on the activity of the cardiomyocytes, through the electrodes of the ECG sensor facing the user's skin, and measure the user's electrocardiogram.

The processor 290 may acquire pressure-related sensor information (e.g., a pressure value) through the pressure sensor. For example, when a user sleeps in a state in which the user wears the electronic device 200 or brings the electronic device 200 into contact with a part of the user's body, the pressure sensor included in the electronic device 200 may be pressed by the user's body according to the user's movement. The pressure sensor may detect this pressure. Also, the processor 290, which has acquired the pressure-related sensor information from the pressure sensor, may determine the degree of movement and a sleeping posture during a user's sleep through the pressure-related sensor information.

The processor 290 may acquire sensor information related to at least one of a user's respiration rate, heart rate, and movement through the ultrasonic sensor. For example, when a user sleeps in a state in which the user wears the electronic device 200, brings the electronic device 200 into contact with a part of the user's body, or locates the electronic device 200 within a predetermined distance from the user, the ultrasonic sensor may measure a distance to a specific object by using a time when radiated ultrasonic waves are reflected and received from the specific object. By radiating the ultrasonic waves at regular time intervals, the ultrasonic sensor may measure a change of the distance to the specific object. The processor 290 may determine at least one of the user's respiration rate, heart rate, and movement, based on this change of the distance.

The processor 290 may acquire sensor information related to a sound provided by the user through the microphone. For example, the microphone may detect a sound provided during a user's sleep, convert the detected sound into an electrical signal, and transmit the same to the processor 290. Also, the processor 290 may determine a snoring symptom or a sleep apnea symptom, based on the characteristics of the sound provided during the user's sleep.

The processor 290 may acquire sensor information (e.g., an illuminance value) related to a brightness of the external environment through the illuminance sensor. For example, the illuminance sensor may measure an amount of light coming from the outside and measure the brightness of the external environment. The illuminance sensor may measure this brightness of the external environment during a user's sleep and forward the same to the processor 290.

The processor 290 may acquire user's sleep information, based on the sensor information acquired through the sensor module 210. The processor 290 may acquire the user's sleep information, based on the sensor information or additional information determined based on the sensor information. For example, the processor 290 may determine a user's sleep state, based on at least one of the degree of movement during a user's sleep, a sleeping posture, a respiration rate, a heart rate, a blood pressure, a blood glucose, a blood volume, an oxygen saturation, a snoring symptom, a sleep apnea symptom, or a brightness of the external environment during sleep, and may provide sleep information related to the determined sleep state.

The processor 290 may also use a weighted average of any combination of the aforementioned sensor module 210 as well as time of day. In certain embodiments, the alarm setting information may also be used. For example, if the sensor module 210 includes a motion sensor, and no/very little motion is detected before an alarm is generated, the foregoing may be deemed the completion of the user's period of sleep.

In this regard, the sleep state may be divided into a rapid eye movement (REM) sleep state and a non-REM (NREM) sleep state. The REM sleep state and the non-REM sleep state proceed according to stages. The non-REM sleep state proceeds into first and second stages of light sleep and third and fourth stages of deep sleep. The REM sleep state may correspond to a fifth stage appearing after passing through the first stage to the fourth stage. The sleep state may be repeated several times from the first stage to the fifth stage.

The first stage is a sleep onset stage, and may occupy about 2 to 5% of a total sleep time. In the first stage, theta waves, which are brain waves, may appear, a body temperature may drop, muscles may be relaxed, and movement may be reduced. The second stage is a sleep onset stage, and may occupy about 45 to 55% of the total sleep time. In the second stage, brain waves, which are a sleep spindle wave and a K complex wave, may appear, and a speed and movement of respiration and pulse may be further lowered than in the first stage. The third stage is a stage of falling into deep sleep, and may occupy about 15 to 20% of the total sleep time in combination with the fourth stage. In the third stage, delta waves, which are brain waves, may appear, and the muscles may be further relaxed, so there may be little movement. The fourth stage is a stage of deep sleep, and may occupy about 15 to 20% of the total sleep time in combination with the third stage. In the fourth stage, high-amplitude brain waves of about 2 Hz or less may appear, there may be hardly a reaction to external stimuli, only a limited muscle may respond, and a blood pressure and a pulse may drop by about 20-30% compared to while awake. The fifth stage is a REM sleep stage, and may occupy about 20 to 25% of the total sleep time. In the fifth stage, high-speed brain waves similar to those in the first stage appear, and the eyeballs may move rapidly.

The various sleep stages can be detected by the sensor module 210 based, at least in part on the user's EKG, snoring detected by a microphone, pulse or heart rate, detected by a PPG, and/or motion as detected by a motion sensor. For example, the processor 290 may determine different levels of motion and heart rate, and when the levels of motion drop below a corresponding level of motion, a particular stage may be detected.

The processor 290 may determine (or predict) a user's biorhythm, based on user's sleep information, such as the time and length of the different stages. The sleep information may include information related to an amount of sleep and information related to a quality of sleep. The information related to the amount of sleep may include, for example, a total sleep time, a time taken to sleep onset, a time taken to a REM sleep stage (e.g., the fifth stage), a time of each stage (e.g., the first stage to the fifth stage) of sleep, or a ratio occupied by the time of each sleep stage among the total sleep time. The information related to the quality of sleep may include, for example, at least one of information indicating a sleep disorder such as snoring or sleep apnea, environmental information affecting sleep such as a brightness or temperature of the external environment during sleep, and user's activity information capable of causing a sleep disorder, such as drinking before sleep, caffeine intake, food intake, or excessive exercise. The processor 290 may determine a biorhythm, based on the information related to the amount of sleep, and correct the determined biorhythm, based on the information related to the quality of sleep.

The processor 290 may determine a biorhythm, based on a total sleep time. In an example, when the total sleep time is in an increasing trend in a specific time duration (e.g., a duration of a day unit), and an increase rate of the total sleep time in the increasing trend is changed from a first magnitude to a second magnitude larger than the first magnitude, the processor 290 may determine the specific time duration as a follicular phase among the biorhythm. In another example, when the total sleep time is changed from the decreasing trend to the increasing trend in the specific time duration, the processor 290 may determine the specific time duration as an ovulatory phase among the biorhythm. In a further example, when the total sleep time is in an increasing trend in the specific time duration, and the increase rate of the total sleep time is a third magnitude smaller than the second magnitude (when it is less than the increase rate of the total sleep time of the follicular phase), the processor 290 may determine the specific time duration as a luteal phase among the biorhythm.

The processor 290 may determine a biorhythm, based on a time taken to sleep onset. In an example, when the time taken to the sleep onset is changed from an increasing trend to a decreasing trend in a specific time duration (e.g., a duration of a day unit), and an increase rate of the time taken to the sleep onset in the increasing trend is greater than or equal to a fourth magnitude, and a decrease rate of the time taken to the sleep onset in the decreasing trend is less than a fifth magnitude, the processor 290 may determine the specific time duration as a follicular phase among the biorhythm. In another example, when the time taken to the sleep onset is changed from the increasing trend to the decreasing trend in the specific time duration, and the increase rate of the time taken to the sleep onset in the increasing trend is a sixth magnitude smaller than the fourth magnitude (is smaller than the increase rate of the time taken to the sleep onset of the follicular phase), and the decrease rate of the time taken to the sleep onset in the decreasing trend is a seventh magnitude larger than the fifth magnitude (when it is larger than the decrease rate of the time taken to the sleep onset of the follicular phase), the processor 290 may determine the specific time duration as an ovulatory phase among the biorhythm. In a further example, when the time taken to the sleep onset in the specific time duration is in the decreasing trend, the processor 290 may determine the specific time duration as a luteal phase among the biorhythm.

The processor 290 may determine a biorhythm, based on a ratio (a ratio of a REM sleep phase) occupied by a time of a REM sleep phase among a total sleep time. In an example, when the ratio occupied by the time of the REM sleep phase among the total sleep time is changed from a decreasing trend to an increasing trend in a specific time duration (e.g., a duration of a day unit), the processor 290 may determine the specific time duration as a follicular phase among the biorhythm. In another example, when the ratio occupied by the time of the REM sleep phase among the total sleep time is in the decreasing trend in the specific time duration, and a decrease rate of the ratio occupied by the time of the REM sleep phase among the total sleep time in the decreasing trend is changed from an eighth magnitude to a ninth magnitude larger than the eighth magnitude, the processor 290 may determine the specific time duration as an ovulatory phase among the biorhythm. In a further example, when the ratio occupied by the time of the REM sleep phase among the total sleep time is changed from the increasing trend to the decreasing trend in the specific time duration, the processor 290 may determine the specific time duration as a luteal phase among the biorhythm.

The processor 290 may determine a biorhythm, based on a time taken to a REM sleep phase. In an example, when the time taken to the REM sleep phase is changed from an increasing trend to a decreasing trend in a specific time duration (e.g., a duration of a day unit), and an increase rate of the time taken to the REM sleep phase in the increasing trend is less than a tenth magnitude, and a decrease rate of the time taken to the REM sleep phase in the decreasing trend is an eleventh magnitude or more, the processor 290 may determine the specific time duration as a follicular phase among the biorhythm. In another example, when the time taken to the REM sleep phase is changed from the decreasing trend to the increasing trend in the specific time duration, the processor 290 may determine the specific time duration as an ovulatory phase among the biorhythm. In a further example, when the time taken to the REM sleep phase is changed from the increasing trend to the decreasing trend in the specific time duration, and an increase rate of the time taken to the REM sleep phase in the increasing trend is a twelfth magnitude higher than the tenth magnitude (is greater than the increase rate of the time taken to the REM sleep stage of the follicular phase), and a decrease rate of the time taken to the REM sleep stage in the decreasing trend is a thirteenth magnitude smaller than the eleventh magnitude (when it is less than the decrease rate of the time taken to the REM sleep stage of the follicular phase), the processor 290 may determine the specific time duration as a luteal phase among the biorhythm.

As described above, the processor 290 may also determine a biorhythm, based on each of a total sleep time, a time taken to sleep onset, a ratio occupied by a time of a REM sleep phase among the total sleep time, and a time taken to the REM sleep phase, and may also determine the biorhythm, based on at least two of the total sleep time, the time taken to the sleep onset, the ratio occupied by the time of the REM sleep phase among the total sleep time, and the time taken to the REM sleep phase. That is, the processor 290 may determine the biorhythm, based on at least one of the total sleep time, the time taken to the sleep onset, the ratio occupied by the time of the REM sleep phase among the total sleep time, or the time taken to the REM sleep phase. In an example, when the total sleep time is in an increasing trend in a specific time duration (e.g., a duration of a day unit), and the time taken to the sleep onset is changed from an increasing trend to a decreasing trend, and the ratio occupied by the time of the REM sleep phase among the total sleep time is changed from the decreasing trend to the increasing trend, and the time taken to the REM sleep phase is changed from the increasing trend to the decreasing trend, the processor 290 may determine the specific time duration as a follicular phase among the biorhythm. In another example, when the total sleep time is changed from the decreasing trend to the increasing trend in the specific time duration, and the time taken to the sleep onset is changed from the increasing trend to the decreasing trend, and the ratio occupied by the time of the REM sleep phase among the total sleep time is in the decreasing trend, and the time taken to the REM sleep phase is changed from the decreasing trend to the increasing trend, the processor 290 may determine the specific time duration as an ovulatory phase among the biorhythm. In a further example, when the total sleep time is in the increasing trend in the specific time duration, and the time taken to the sleep onset is in the decreasing trend, and the ratio occupied by the time of the REM sleep phase among the total sleep time is changed from the increasing trend to the decreasing trend, and the time taken to the REM sleep phase is changed from the increasing trend to the decreasing trend, the processor 290 may determine the specific time duration as a luteal phase among the biorhythm.

According to an embodiment, when determining the follicular phase, ovulatory phase, or luteal phase of the biorhythm, the processor 290 may determine in consideration of the order of the follicular phase, the ovulatory phase, and the luteal phase. For example, when a characteristic of at least one of the total sleep time, the time taken to the sleep onset, the ratio occupied by the time of the REM sleep phase among the total sleep time, or the time taken to the REM sleep phase is different from a characteristic appearing in each of the follicular phase, the ovulatory phase and the luteal phase, the processor 290 may determine the biorhythm in consideration of the follicular phase, the ovulatory phase, and the luteal phase. In an example, even if the ratio occupied by the time of the REM sleep phase among the total sleep time is changed from the decreasing trend to the increasing trend in the specific time duration (e.g., the duration of the day unit), when a time duration in which this characteristic appears is between the ovulatory phase and the luteal phase, the processor 290 may not determine the specific time duration as the follicular phase among the biorhythm.

The processor 290 may correct the determined biorhythm, based on at least one of information related to a quality of sleep, for example, information indicating a sleep disorder such as snoring or sleep apnea, environmental information affecting sleep such as a brightness or temperature of an external environment during sleep, and user's activity information capable of causing a sleep disorder, such as drinking before sleep, caffeine intake, food intake, or excessive exercise. In an example, when information indicating the sleep apnea is less than a specified value (reduces a sleep apnea symptom), the processor 290 may adjust the time duration determined as the luteal phase of the biorhythm. For example, the processor 290 may increase the time duration determined as the luteal phase. In another example, when at least one of the brightness and temperature of the external environment during sleep is greater than or equal to a specified value, because a phenomenon in which a user fails to get a deep sleep or wakes up frequently during REM sleep may temporarily occur, the processor 290 may correct at least one value among the determined total sleep time, the time taken to the sleep onset, the ratio occupied by the time of the REM sleep phase among the total sleep time, or the time taken to the REM sleep stage (e.g., increase the time taken to the sleep onset, and decrease the total sleep time, the ratio occupied by the time of the REM sleep stage among the total sleep time, and the time taken to the REM sleep stage), and correct the biorhythm, based on the corrected value. In a further example, when it is determined that a user has consumed caffeine before sleep based on the user's activity information, because a phenomenon in which the time taken to the sleep onset increases, a REM sleep decreases, and frequent wake is made during sleep may temporarily occur, the processor 290 may correct at least one value among the determined total sleep time, the time taken to the sleep onset, the ratio occupied by the time of the REM sleep phase among the total sleep time, or the time taken to the REM sleep phase (e.g., increase the time taken to the sleep onset, and decrease the total sleep time, the ratio occupied by the time of the REM sleep phase among the total sleep time, or the time taken to the REM sleep phase), and may correct the biorhythm, based on the corrected value. In a yet another example, when it is determined that the user drank before sleep based on the user's activity information, because the time taken to the sleep onset is shortened but the REM sleep temporarily decreases, the processor 290 may correct at least one value among the determined total sleep time, the time taken to the sleep onset, the ratio occupied by the time of the REM sleep phase among the total sleep time, or the time taken to the REM sleep phase (e.g., decrease the time taken to the sleep onset and the ratio occupied by the time of the REM sleep phase among the total sleep time), and correct the biorhythm, based on the corrected value.

According to an embodiment, when the sensor module 210 further includes a temperature sensor, the processor 290 may determine (or correct) a biorhythm, based on a user's body temperature measured through the temperature sensor. In an example, the processor 290 may determine the biorhythm by using a basal body temperature method being based on the user's body temperature. In another example, the processor 290 may correct the biorhythm determined based on sleep information, by using the biorhythm determined using the basal body temperature method.

The processor 290 may correct a determined biorhythm, based on a history of sleep information. For example, in a state in which information indicating a sleep disorder such as snoring or sleep apnea is less than a specified value (an effect on sleep is insignificant) or does not exist for a previously specified period being based on a current time point, when newly acquired information indicating a sleep disorder is greater than or equal to a specified value, the processor 290 may determine whether the sleep disorder is temporary. Also, when it is determined that the sleep disorder is temporary, the processor 290 may correct sleep information (e.g., at least one of the total sleep time, the time taken to the sleep onset, the ratio occupied by the time of the REM sleep stage among the total sleep time, or the time taken to the REM sleep stage), and may correct the biorhythm, based on the corrected value. In another embodiment, when it is determined that the sleep disorder is temporary, the processor 290 may ignore the corresponding sleep information. For example, the processor 290 may not use the sleep information determined as the temporary sleep disorder, in determining the biorhythm. The processor 290 may determine the continuity of the sleep disorder, based on at least one of environmental information affecting sleep, such as a brightness or temperature of the external environment during sleep, and user's activity information capable of causing a sleep disorder such as drinking before sleep, caffeine intake, food intake, or excessive exercise. For example, when a user drinks alcohol before sleep, consumes caffeine, consumes food, or does excessive exercise, the processor 290 may determine that the sleep order is temporary. In this regard, the processor 290 may acquire user's activity information such as drinking, caffeine intake, food intake, or exercise, through a user input.

The processor 290 may present information on the determined biorhythm to a user. The processor 290 may display information on the biorhythm on the display 250. According to another embodiment, the processor 290 may output the information on the biorhythm as a sound through a sound output device. According to a further embodiment, the processor 290 may output a vibration corresponding to the information on the biorhythm through a haptic module (e.g., the haptic module 179 of FIG. 1). In some embodiment, the processor 290 may transmit the information on the biorhythm to an external electronic device through the communication module 230.

The processor 290 may receive sensor information from an external electronic device through the communication module 230. The external electronic device may be, for example, an electronic device that is in a state of being worn by the user or being in contact with a part of the user's body. Also, the external electronic device may include at least one of a motion sensor, a PPG sensor, a pressure sensor, an ultrasonic sensor, a microphone, or an illuminance sensor. The processor 290 may acquire user's sleep information, based on the sensor information received from the external electronic device, and determine a user's biorhythm, based on the acquired sleep information. In some embodiment, the processor 290 may acquire the user's sleep information, based on the sensor information received from the external electronic device and the sensor information acquired through the sensor module 210, and determine a user's biorhythm, based on the acquired sleep information. In another embodiment, when acquiring sensor information through the sensor module 210 and receiving sensor information from the external electronic device, the processor 290 may synchronize the sensor information acquired through the sensor module 210 and the sensor information received from the external electronic device. In this case, the processor 290 may acquire the user's sleep information, based on the synchronized sensor information, and determine the user's biorhythm, based on the acquired sleep information.

The processor 290 may store at least one of the sensor information, the sleep information, and the information on the biorhythm in the memory 270. The processor 290 may accumulate at least one of the sensor information, the sleep information, and the information on the biorhythm in the memory 270 for a specified period and build a database.

The processor 290 may determine a change of a biorhythm, based on a database of a user's biorhythm. Also, when an amount of change of the biorhythm is greater than or equal to a specified magnitude, the processor 290 may present a notification to a user. For example, the processor may display notification information on the amount of change of the biorhythm on the display 250. In some embodiment, when the amount of change of the biorhythm is greater than or equal to a specified magnitude, the processor 290 may include at least one of a content of recommending medical treatment or a content of recommending a hospital capable of offering medical treatment, in the notification information.

The processor 290 may manage at least one of the sensor information, the sleep information, and the information on the biorhythm in a secure area (e.g., a trusted execution environment (TEE)). The processor 290 may secure (e.g., encrypt) at least one of the sensor information, the sleep information, and the information on the biorhythm and store it in the memory 270. Or, the processor 290 may store at least one of the sensor information, the sleep information, and the information on the biorhythm, in secure hardware physically separated from the processor 290.

As described above, according to certain embodiments, an electronic device (e.g., the electronic device 101 or the electronic device 200) may include a sensor module (e.g., the sensor module 176 or the sensor module 210), a processor (e.g., the processor 120 or the processor 290) operatively connected to the sensor module, and a memory (e.g., the memory 130 or the memory 270) operatively connected to the processor. The memory may store instructions that, when executed, cause the processor to perform a plurality of operations comprising: acquiring sensor information through the sensor module, determining sleep information of a user, based on the sensor information, and determining a biorhythm of the user, based on the sleep information.

According to certain embodiments, the sensor information may include at least one of information related to a movement of the electronic device, information related to a pressure applied from the outside of the electronic device, a user's respiration rate, heart rate, blood pressure, blood glucose, blood volume and/or oxygen saturation, information related to a sound provided by a user, or information related to a brightness of an external environment of the electronic device.

According to certain embodiments, the sleep information may include first information related to an amount of sleep, wherein the first information related to an amount of sleep comprises at least one of an amount of time taken to sleep onset, a time taken to a REM sleep stage, a time of each sleep stage, a total sleep time, or a ratio of the time of each sleep stage to the total sleep time.

According to certain embodiments, wherein the plurality of operations further comprises determining a time duration of each sleep stage, based on the first information.

According to certain embodiments, the sleep information may further include second information related to a quality of sleep including information indicating a sleep disorder, environmental information affecting the sleep, and user's activity information before the sleep.

According to certain embodiments, the plurality of operations further comprises adjusting the determined time duration of each sleep stage, based on the second information.

According to certain embodiments, the electronic device may further include a display (e.g., the display 160 or the display 250), and the plurality of operations further comprises displaying a user interface including information indicating the determined biorhythm on the display.

According to certain embodiments, wherein the plurality of operations further comprises setting a graphic characteristic of an element corresponding to an interest period in the biorhythm, to be different from graphic characteristics of other elements.

According to certain embodiments, the electronic device may further include a display (e.g., the display 160 or the display 250), and wherein the plurality of operations further comprises determining an amount of change of the biorhythm, based on the determined biorhythm for a specified period, and when the amount of change of the biorhythm is greater than or equal to a specified magnitude, display notification information on the amount of change on the display.

According to certain embodiments, the plurality of operations further comprises storing at least one of the sensor information, the sleep information, and information on the biorhythm in a secure area, or a secure hardware physically separated from the processor.

Figure 3:
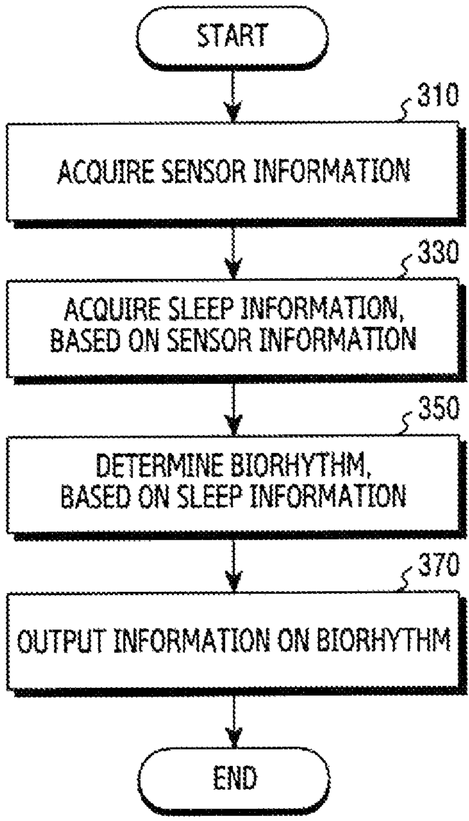
FIG. 3 is a diagram illustrating an operating method of an electronic device related to the determination of a biorhythm according to an embodiment of the present invention.

FIG. 3 is a diagram illustrating an operating method of an electronic device related to the determination of a biorhythm according to an embodiment of the present invention.

Referring to FIG. 3, in operation 310, a processor (e.g., the processor 290 of FIG. 2) of the electronic device (e.g., the electronic device 200 of FIG. 2) may acquire sensor information from the sensor module 210. The processor 290 may acquire the sensor information through a sensor module (e.g., the sensor module 210 of FIG. 2) included in the electronic device 200. According to another embodiment, the processor 290 may acquire the sensor information from an external electronic device connected through a communication module (e.g., the communication module 230 of FIG. 2). According to a further embodiment, the processor may acquire first sensor information through the sensor module 210, and acquire second sensor information from the external electronic device through the communication module 230. In some embodiment, the processor 290 may synchronize the first sensor information and the second sensor information.

The sensor information form the sensor module 210 may include, for example, at least one of information related to a movement of the electronic device acquired through a motion sensor, information related to at least one of a user's heart rate, blood pressure, blood glucose, blood volume, and oxygen saturation acquired through a PPG sensor, information related to a pressure acquired through a pressure sensor, information related to at least one of a user's respiration rate, heart rate, or movement acquired through an ultrasonic sensor, information related to a sound provided from a user acquired through a microphone, or information related to a brightness of the external environment acquired through an illuminance sensor, time of day, and alarm settings.

In operation 330, the processor may acquire sleep information, based on the sensor information. The processor may acquire user's sleep information, based on the sensor information or additional information determined based on the sensor information. For example, the processor may determine a user's sleep state, based on at least one of a user's movement level during sleep, a sleeping posture, a respiration rate, a heart rate, a blood pressure, a blood glucose, a blood volume, an oxygen saturation, a snoring symptom, a sleep apnea symptom, or a brightness of the external environment during sleep, and may provide sleep information related to the determined sleep state.

The sleep information may include information related to an amount of sleep and information related to a quality of sleep. The information related to the amount of sleep may include, for example, at least one of a total sleep time, a time taken to sleep onset, a time taken to a REM sleep stage, a time of each sleep stage, or a ratio occupied by the time of each sleep stage among the total sleep time. The information related to the quality of sleep may include, for example, at least one of information indicating a sleep disorder such as snoring or sleep apnea, environmental information affecting sleep such as a brightness or temperature of the external environment during sleep, and user's activity information capable of causing a sleep disorder such as drinking before sleep, caffeine intake, food intake or excessive exercise.

In operation 350, the processor may determine a biorhythm, based on the sleep information. The processor may determine a user's biorhythm, based on the information related to the amount of sleep among the sleep information. The processor may determine the biorhythm, based on at least one of a total sleep time, a time taken to sleep onset, a ratio occupied by a time of a REM sleep phase among the total sleep time, or a time taken to the REM sleep phase. In an example, when the total sleep time is in an increasing trend in a specific time duration (e.g., a duration of a day unit), and the time taken to the sleep onset is changed from the increasing trend to a decreasing trend, and the ratio occupied by the time of the REM sleep phase among the total sleep time is changed from the decreasing trend to the increasing trend, and the time taken to the REM sleep stage is changed from the increasing trend to the decreasing trend, the processor may determine the specific time duration as a follicular phase among the biorhythm. In another example, when the total sleep time is changed from the decreasing trend to the increasing trend in a specific time duration, and the time taken to the sleep onset is changed from the increasing trend to the decreasing trend, and the ratio occupied by the time of the REM sleep phase among the total sleep time is in the decreasing trend, and the time taken to the REM sleep phase is changed from the decreasing trend to the increasing trend, the processor may determine the specific time duration as an ovulatory phase among the biorhythm. In a further example, when the total sleep time is in the increasing trend in the specific time duration, and the time taken to the sleep onset is in the decreasing trend, and the ratio occupied by the time of the REM sleep phase among the total sleep time is changed from the increasing trend to the decreasing trend, and the time taken to the REM sleep phase is changed from the increasing trend to the decreasing trend, the processor may determine the specific time duration as a luteal phase among the biorhythm.

According to an embodiment, when determining the follicular phase, ovulatory phase, or luteal phase of the biorhythm, the processor may determine in consideration of the order of the follicular phase, the ovulatory phase, and the luteal phase. For example, when a characteristic of at least one of the total sleep time, the time taken to the sleep onset, the ratio occupied by the time of the REM sleep phase among the total sleep time, or the time taken to the REM sleep phase is different from a characteristic appearing in each of the follicular phase, the ovulatory phase and the luteal phase, the processor may determine the biorhythm in consideration of the order of the follicular phase, the ovulatory phase, and the luteal phase.

The processor may correct the determined biorhythm, based on a history of the sleep information. For example, in a state where information indicating a sleep disorder such as snoring or sleep apnea is less than a specified value (an effect on sleep is insignificant) or does not exist for a previously specified period based on a current time point, when information indicating a newly acquired sleep disorder is greater than or equal to the specified value, the processor may determine whether the sleep disorder is temporary. Also, when it is determined that the sleep disorder is temporary, the processor may correct the sleep information (e.g., at least one of the total sleep time, the time taken to the sleep onset, the ratio occupied by the time of the REM sleep phase among the total sleep time, or the time taken to the REM sleep phase), and may correct the biorhythm, based on the corrected value. In this regard, the processor may determine the continuity of the sleep disorder, based on at least one of the environmental information affecting sleep such as a brightness or temperature of the external environment during sleep, and user's activity information capable of causing a sleep disorder such as drinking before sleep, caffeine intake, food intake, or excessive exercise. For example, when a user drinks alcohol, consumes caffeine, consumes food, or does excessive exercise before sleep, the processor may determine that the sleep disorder is temporary. The processor may acquire user's activity information such as drinking, caffeine intake, food intake, or exercise, through a user input. In another embodiment, when a difference between the sleep information and sleep information for a previous specified period based on a current time is greater than or equal to a specified magnitude, the processor may ignore the sleep information (not used for determining the biorhythm).

The processor may correct the determined biorhythm, based on the information related to the quality of sleep among the sleep information. In an example, when information indicating sleep apnea is less than a specified value, the processor may adjust a time duration determined as a luteal phase of the biorhythm. In an example, the processor may increase the time duration determined as the luteal phase. In another example, when at least one of a brightness and temperature of the external environment during sleep is greater than or equal to a specified value, the processor may correct the acquired sleep information (e.g., increase the time taken to the sleep onset, and decrease the total sleep time, the ratio occupied by the time of the REM sleep phase among the total sleep time, and the time taken to the REM sleep phase), and correct the biorhythm, based on the corrected sleep information. In a further example, when it is determined that a user has consumed caffeine before sleep based on the user's activity information, the processor may correct the acquired sleep information (e.g., increase the time taken to the sleep onset, and decrease the total sleep time, the ratio occupied by the time of the REM sleep phase among the total sleep time, and the time taken to the REM sleep phase), and correct the biorhythm, based on the corrected sleep information. In a yet another example, when it is determined that the user has drunk before sleep based on the user's activity information, the processor may correct the acquired sleep information (e.g., decrease the time taken to the sleep onset and the ratio occupied by the time of the REM sleep phase among the total sleep time), and correct the biorhythm, based on the corrected sleep information.

In operation 370, the processor may output information on the biorhythm. For example, the processor may present the information on the determined biorhythm to a user. The processor may display the information on the biorhythm on a display (e.g., the display 250 of FIG. 2). According to another embodiment, the processor may output the information on the biorhythm by a sound through a sound output device (e.g., the sound output module 155 of FIG. 1). According to a further embodiment, the processor may output a vibration corresponding to the information on the biorhythm through a haptic module (e.g., the haptic module 179 of FIG. 1). In some embodiment, the processor may transmit the information on the biorhythm to an external electronic device through the communication module.

The processor may store at least one of the sensor information, the sleep information, and the information on the biorhythm in a memory (e.g., the memory 270 of FIG. 2). For example, the processor may accumulate at least one of the sensor information, the sleep information, and the information on the biorhythm in the memory for a specified period, and build a database. Also, the processor may determine a change of a biorhythm, based on a database of the user's biorhythm. Accordingly, when an amount of change of the biorhythm is greater than or equal to a specified magnitude, the processor may present a notification to the user. Also, the processor may check a user's sleep pattern, based on a database of the user's sleep information, and may determine whether a user's sleep state of the acquired sleep information deviates from an existing sleep pattern. When the user's sleep state of the acquired sleep information deviates from the existing sleep pattern, the processor may determine whether a pattern deviation phenomenon of the sleep state of the acquired sleep information is temporary. In an example, the processor may determine whether the pattern deviation phenomenon of the sleep state is temporary based on at least one of environmental information affecting sleep such as a brightness or temperature of an external environment during sleep, and user's activity information capable of causing a sleep order such as drinking before sleep, caffeine intake, food intake, or excessive exercise. When it is determined that the pattern deviation phenomenon of the sleep state is temporary, the processor may correct the acquired sleep information, based on the existing sleep information, and correct the user's biorhythm, based on the corrected sleep information.

The processor may acquire the user's activity information through a user input. The user's activity information may include at least one of information on drinking before sleep, caffeine intake, food intake, and exercise performance. Also, the processor may acquire information on a user's health state through a user input and reflect it on the sleep information or the biorhythm as well. The information on the user's health state may include, for example, at least one of menstrual flow, menstrual pain, back pain, acne, chest swelling, appetite, constipation, diarrhea, headache, blood pressure, dizziness, sweat, premenstrual syndrome, nausea, cervical mucus, itching, insomnia, fatigue, body aches, mood, BMI (weight/height), smoking, pregnancy test/ovulation test results, sex date, or information on whether or not to take hormonal/contraceptive pills.

As described above, according to certain embodiments, a biorhythm determination method of an electronic device (e.g., the electronic device 101 or the electronic device 200) may include acquiring (e.g., operation 310) sensor information through a sensor module (e.g., the sensor module 176 or the sensor module 210) included in the electronic device, determining (e.g., operation 330) sleep information of a user, based on the sensor information, determining (e.g., operation 350) a biorhythm of the user, based on the sleep information, and displaying information based on the biorhythm of the user on a display of the electronic device.

According to certain embodiments, the sensor information may include at least one of information related to a movement of the electronic device, information related to a pressure applied from the outside of the electronic device, a user's respiration rate, heart rate, blood pressure, blood glucose, blood volume and/or oxygen saturation, information related to a sound provided by a user, or information related to a brightness of an external environment of the electronic device.

According to certain embodiments, the sleep information may include first information related to an amount of sleep wherein the first information related to an amount of sleep comprises at least one of an amount time taken to sleep onset, a time taken to a REM sleep stage, a time of each sleep stage, a total sleep time, or a ratio of the time of each sleep stage to the total sleep time.

According to certain embodiments, determining the biorhythm may include determining a time duration of each sleep stage, based on the first information.

According to certain embodiments, the sleep information may further include second information related to a quality of sleep including information indicating a sleep disorder, environmental information affecting the sleep, and user's activity information before the sleep.

According to certain embodiments, determining the biorhythm may further include adjusting the determined time duration of each sleep stage, based on the second information.

According to certain embodiments, the biorhythm determination method may further include displaying a user interface including the determined information on the biorhythm on a display (e.g., the display 160 or the display 250) included in the electronic device.

According to certain embodiments, displaying the user interface may include setting a graphic characteristic of an element corresponding to an interest period included in the biorhythm among elements of a specified time unit included in the user interface, to be different from graphic characteristics of other elements.

According to certain embodiments, the biorhythm determination method may further include determining an amount of change of the biorhythm, based on information on the biorhythm for a specified period, and when the amount of change of the biorhythm is greater than or equal to a specified magnitude, displaying notification information on the amount of change of the biorhythm on a display included in the electronic device.

According to certain embodiments, the biorhythm determination method may further include storing at least one of the sensor information, the sleep information, and information on the biorhythm in a secure area of a processor (e.g., the processor 120 or the processor 290) included in the electronic device, or a secure hardware physically separated from the processor.

Figure 4:
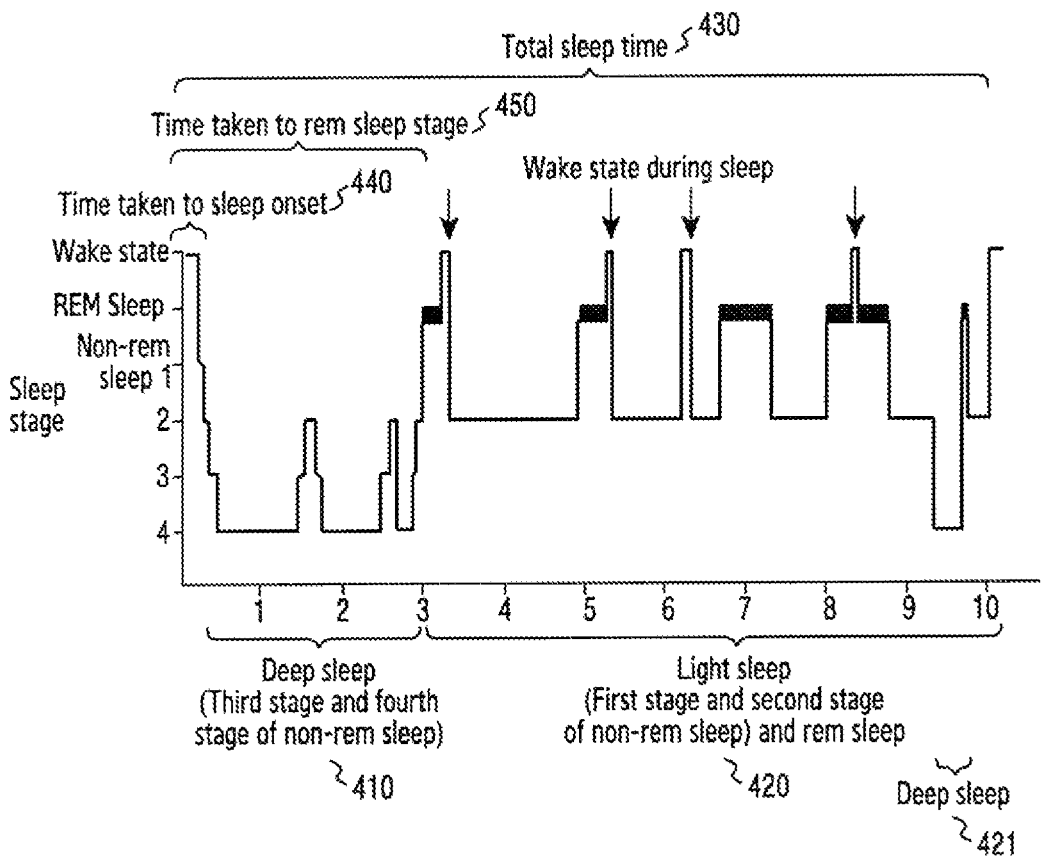
FIG. 4 is a diagram for explaining sleep information according to an embodiment of the present invention.
Figure 5:
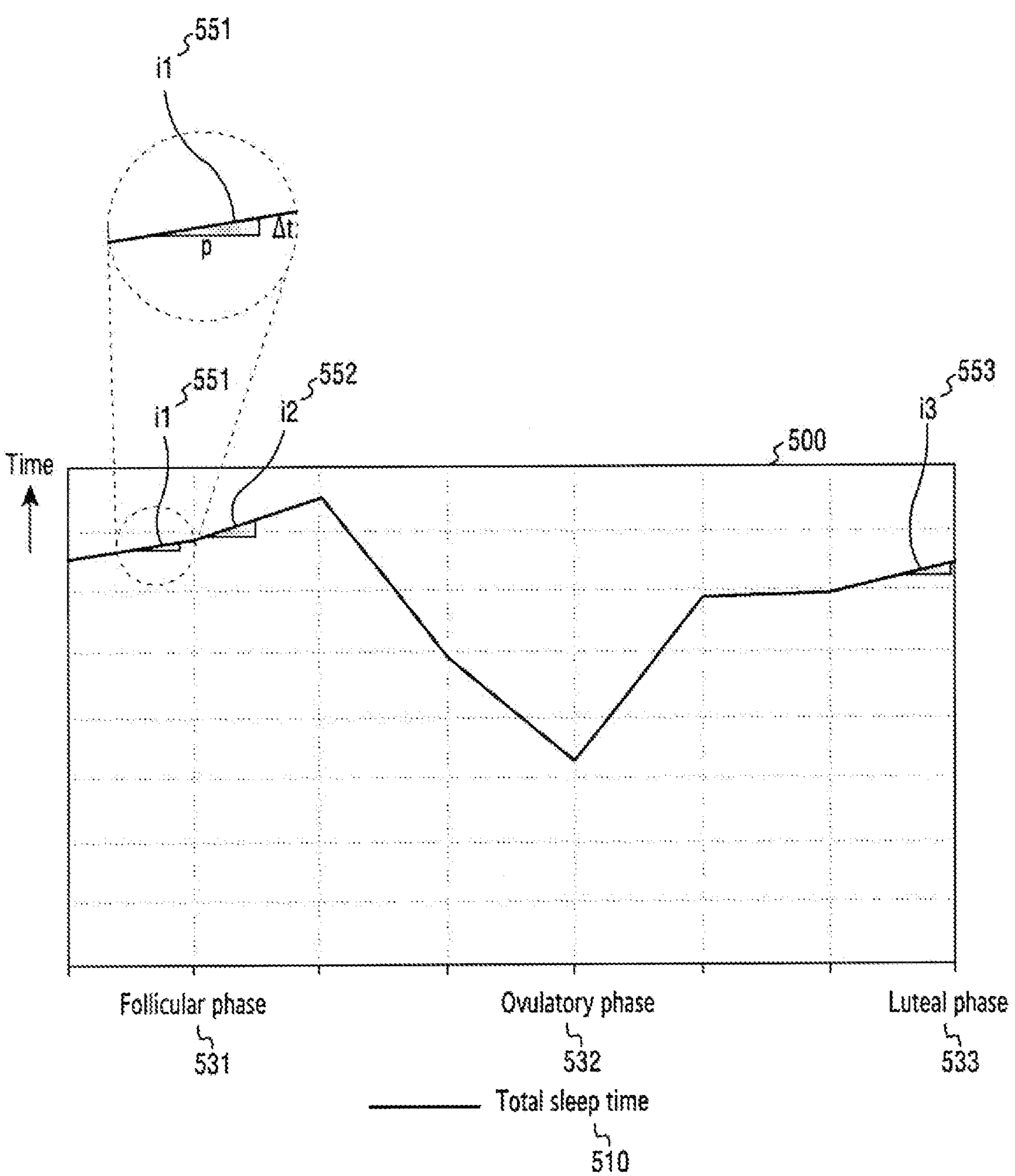
FIG. 5 is a diagram for explaining a relationship between a total sleep time and a biorhythm according to an embodiment of the present invention.
Figure 6:
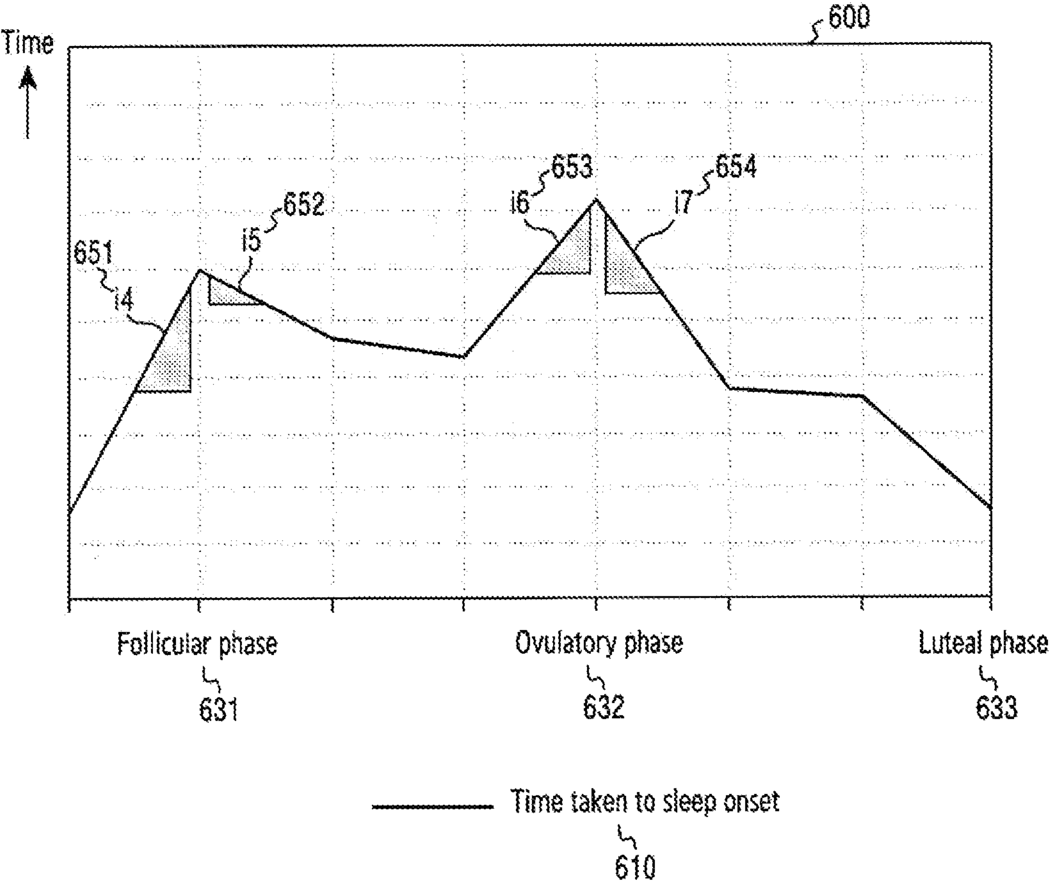
FIG. 6 is a diagram for explaining a relationship between a time taken to sleep onset and a biorhythm according to an embodiment of the present invention.
Figure 7:
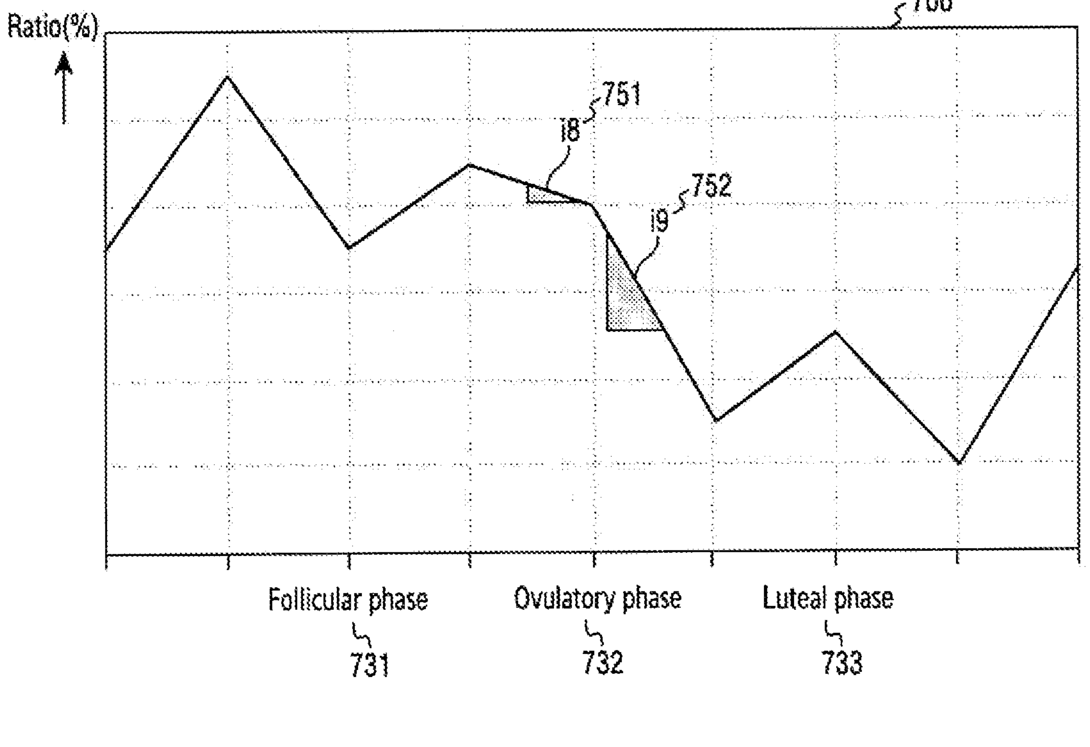
FIG. 7 is a diagram for explaining a relationship between a ratio of a REM sleep phase time to a total sleep time and a biorhythm according to an embodiment of the present invention.
Figure 8:
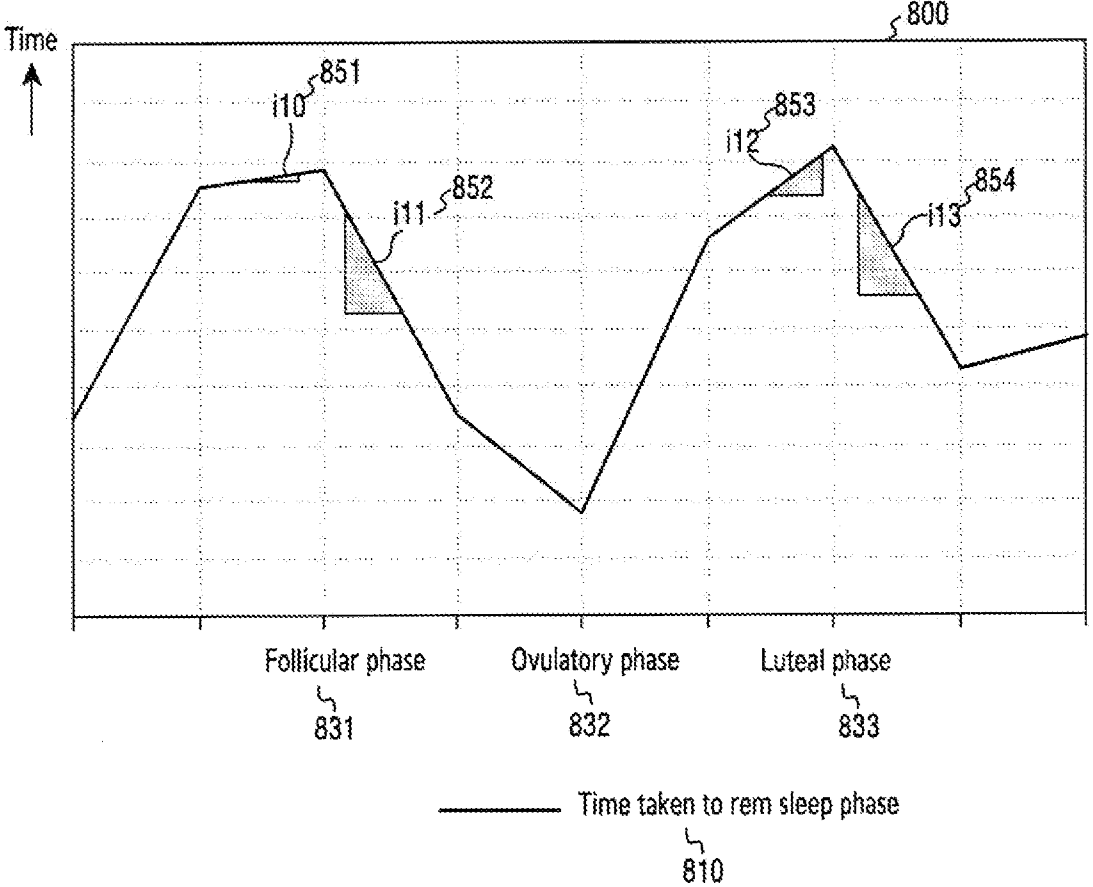
FIG. 8 is a diagram for explaining a relationship between a time taken to a REM sleep phase and a biorhythm according to an embodiment of the present invention.

FIG. 4 is a diagram for explaining sleep information according to an embodiment of the present invention. FIG. 5 is a diagram for explaining a relationship between a total sleep time and a biorhythm according to an embodiment of the present invention. FIG. 6 is a diagram for explaining a relationship between a time taken to sleep onset and the biorhythm according to an embodiment of the present invention. FIG. 7 is a diagram for explaining a relationship between a ratio occupied by a time of a REM sleep phase among a total sleep time and the biorhythm according to an embodiment of the present invention. FIG. 8 is a diagram for explaining a relationship between a time taken to the REM sleep phase and the biorhythm according to an embodiment of the present invention.

Referring to FIG. 4, horizontal axis measures time in hours, while the vertical axis indicates REM sleep state or wake state. A sleep state may be divided into a REM sleep state and a non-REM sleep state. The REM sleep state and the non-REM sleep state proceed according to sleep stages. The non-REM sleep state proceeds according to a first stage and a second stage, which are a light sleep 420, and a third stage and a fourth stage, which are a deep sleep 410 and 421. The REM sleep state may correspond to a fifth stage appearing after passing through the first stage to the fourth stage. The sleep state may be repeated several times from the first stage to the fifth stage.

The first stage is a sleep onset stage, and may occupy about 2 to 5% of a total sleep time 430. In the first stage, theta waves, which are brain waves, may appear, a body temperature may drop, muscles may be relaxed, and movement may be reduced. The second stage is a sleep onset stage, and may occupy about 45 to 55% of the total sleep time 430. In the second stage, brain waves, which are a sleep spindle wave and a K complex wave, may appear, and a speed and movement of respiration and pulse may be further lowered than in the first stage. The third stage is a stage of falling into deep sleep, and may occupy about 15 to 20% of the total sleep time 430 in combination with the fourth stage. In the third stage, delta waves, which are brain waves, may appear, and the muscles may be further relaxed, so there is little movement. The fourth stage is a stage of deep sleep, and may occupy about 15 to 20% of the total sleep time 430 in combination with the third stage. In the fourth stage, high-amplitude brain waves of about 2 Hz or less may appear, there may be hardly a reaction to external stimuli, only a limited muscle may respond, and a blood pressure and a pulse may drop by about 20-30% compared to while awake. The fifth stage is a REM sleep stage, and may occupy about 20 to 25% of the total sleep time 430. In the fifth stage, high-speed brain waves similar to those in the first stage may appear, and the eyeballs may move rapidly.

FIG. 5 shows a first graph 500 of the relationship between a total sleep time 510 (e.g., the total sleep time 430 of FIG. 4) and a biorhythm phases. the biorhythm may be determined based on the total sleep time 510. The horizontal axis measures days while the horizontal axis measures total sleep time. The menstrual cycle includes a follicular phase 531, an ovulatory phase 532, and a luteal phase 533.

The follicular phase 531 is characterized by trend of increased sleep. According to an embodiment, when the total measured sleep time 510 is in an increasing trend on a day by day basis, and an increase rate the total sleep time 510 in the increasing trend is changed from a first magnitude (il) 551 to a second magnitude (i2) 552, the time period can be deemed the follicular phase 531. In this regard, the increase rate (or decrease rate) may be calculated as an increase amount (decrease amount) (Δt) in a unit time duration (p). Even in the following description, a calculation method for the increase rate (or decrease rate) may be equally applied.

The ovulatory phase 532 is characterized as having a sharp decrease in total sleep time, followed by a sharp increase in total sleeping time prior to a "leveling off." According to an embodiment, when the total sleep time 510 is changed from an increasing trend to a sharply decreasing trend (a slope exceeding a predetermined threshold), followed by a sharply increasing trend (a slope exceeding another predetermined threshold) in the specific time duration, the specific time duration may be included in an ovulatory phase 532 among the biorhythm.

The luteal phase is characterized by a leveling off of the sleep time followed by a slowly rising trend in sleep time. According to an embodiment, when the total sleep time 510 is in an increasing trend in the specific time duration, and the increase rate of the total sleep time 510 is a third magnitude (i3) 553 smaller than the second magnitude 552 (e.g., is less than the increase rate the total sleep time 510 of the follicular phase 531), the specific time duration may be included in a luteal phase 533 among the biorhythm.

Referring to a second graph 600 showing a relationship between a time (sleep latency) 610 taken to sleep onset (e.g., the time 440 taken to the sleep onset of FIG. 4) and a biorhythm shown in FIG. 6, the biorhythm may be determined based on the time 610 taken to the sleep onset. Here, the time 610 taken to the sleep onset may be from a time when a user intends to sleep to a time when the user actually falls asleep.

According to an embodiment, when the time 610 taken to the sleep onset is changed from an increasing trend to a decreasing trend in a specific time duration (e.g., a duration of a day unit), and an increase rate of the time 610 taken to the sleep onset in the increasing trend is a fourth magnitude (i4) 651 or more, and a decrease rate of the time 610 taken to the sleep onset in the decreasing trend is less than a fifth magnitude (i5) 652, the specific time duration may be included in a follicular phase 631 (e.g., the follicular phase 531 of FIG. 5) among the biorhythm.

According to an embodiment, when the time 610 taken to the sleep onset is changed from the increasing trend to the decreasing trend in the specific time duration, and the increase rate of the time 610 taken to the sleep onset in the increasing trend is a sixth magnitude (i6) 653 smaller than the fourth magnitude 651 (e.g., is less than the increase rate of the time 610 taken to the sleep onset of the follicular phase 631), and the decrease rate of the time 610 taken to the sleep onset in the decreasing trend is a seventh magnitude (i7) 654 greater than the fifth magnitude 652 (e.g., is greater than the decrease rate of the time 610 taken to the sleep onset of the follicular phase 631), the specific time duration may be included in an ovulatory phase 632 (e.g., the ovulatory phase 532 of FIG. 5) among the biorhythm.

According to an embodiment, if the time 610 taken to the sleep onset is in the decreasing trend in the specific time duration, the specific time duration may be included in a luteal phase 633 (e.g., the luteal phase 533 of FIG. 5) among the biorhythm.

Referring to a third graph 700 showing a relationship between a ratio 710 occupied by a time of a REM sleep phase (a ratio (%) of a REM sleep phase) among the total sleep time 430 and a biorhythm shown in FIG. 7, the biorhythm may be determined based on the ratio 710 occupied by the time of the REM sleep phase among the total sleep time 430.

According to an embodiment, when the ratio 710 occupied by the time of the REM sleep phase among the total sleep time 430 is changed from a decreasing trend to an increasing trend in a specific time duration (e.g., a duration of a day unit), the specific time duration may be included in a follicular phase 731 (e.g., the follicular phase 531 of FIG. 5 or the follicular phase 631 of FIG. 6) among the biorhythm.

According to an embodiment, when the ratio 710 occupied by the time of the REM sleep phase among the total sleep time 430 is in a decreasing trend in the specific time duration, and a decrease rate of the ratio 710 occupied by the time of the REM sleep phase among the total sleep time 430 in the decreasing trend is changed from an eighth magnitude (i8) 751 to a ninth magnitude (i9) 752 greater than the eighth magnitude 751, the specific time duration may be included in an ovulatory phase 732 (e.g., the ovulatory phase 532 of FIG. 5 or the ovulatory phase 632 of FIG. 6) among the biorhythm.

According to an embodiment, when the ratio 710 occupied by the time of the REM sleep phase among the total sleep time 430 is changed from the increasing trend to the decreasing trend in the specific time duration, the specific time duration may be included in a luteal phase 733 (e.g., the luteal phase 533 of FIG. 5 or the luteal phase 633 of FIG. 6) among the biorhythm.

Referring to a fourth graph 800 showing a relationship between a time (REM latency) 810 taken to a REM sleep stage (e.g., the time 450 taken to the REM sleep stage of FIG. 4) and a biorhythm shown in FIG. 8, the biorhythm may be determined based on the time 810 taken to the REM sleep phase. Here, the time 810 taken to the REM sleep stage may be a time from sleep onset to the REM sleep stage.

According to an embodiment, when the time 810 taken to the REM sleep phase is changed from an increasing trend to a decreasing trend in a specific time duration (e.g., a duration of a day unit), and an increase rate of the time 810 taken to the REM sleep phase in the increasing trend is less than a tenth magnitude (i10) 851, and a decrease rate of the time 810 taken to the REM sleep phase in the decreasing trend is equal to or greater than an eleventh magnitude (i11) 852, the specific time duration may be included in a follicular phase 831 (e.g., the follicular phase 531 of FIG. 5, the follicular phase 631 of FIG. 6, or the follicular phase 731 of FIG. 7) among the biorhythm.

According to an embodiment, when the time 810 taken to the REM sleep phase is changed from the decreasing trend to the increasing trend in the specific time duration, the specific time duration may be included in an ovulatory phase 832 (e.g., the ovulatory phase 532 of FIG. 5, the ovulatory phase 632 of FIG. 6, or the ovulatory phase 732 of FIG. 7) among the biorhythm.

According to an embodiment, when the time 810 taken to the REM sleep stage is changed from the increasing trend to the decreasing trend in the specific time duration, and an increase rate of the time 810 taken to the REM sleep stage in the increasing trend is a twelfth magnitude (i12) 853 greater than the tenth magnitude 851 (e.g., is greater than the increase rate of the time 810 taken to the REM sleep stage of the follicular phase 831), and a decrease rate of the time 810 taken to the REM sleep stage in the decreasing trend is a thirteenth magnitude (i13) 854 smaller than the eleventh magnitude 852 (e.g., is smaller than the decrease rate of the time 810 taken to the REM sleep stage of the follicular phase 831), the specific time duration may be included in a luteal phase 833 (e.g., the luteal phase 533 of FIG. 5, the luteal phase 633 of FIG. 6, or the luteal phase 733 of FIG. 7) among the biorhythm.

In the above description, although a description has been made for the method of determining the biorhythm based on each of the total sleep time 510, the time 610 taken to the sleep onset, the ratio 710 occupied by the time of the REM sleep phase among the total sleep time, and the time 810 taken to the REM sleep phase, the present invention is not limited thereto. According to certain embodiments, the biorhythm may be determined based on at least two factors among the total sleep time 510, the time 610 taken to the sleep onset, the ratio 710 occupied by the time of the REM sleep phase among the total sleep time, and the time 810 taken to the REM sleep phase. That is, the biorhythm may be determined, based on at least one of the total sleep time 510, the time 610 taken to the sleep onset, the ratio 710 occupied by the time of the REM sleep phase among the total sleep time, or the time 810 taken to the REM sleep phase. When the biorhythm is determined based on at least two of the above factors, at least two of the first graph 500, the second graph 600, the third graph 700 and the fourth graph 800 shown in FIG. 5 to FIG. 8 may be referred to in a combined form.

According to an embodiment, when the total sleep time 510 is in an increasing trend in a specific time duration (e.g., a duration of a day unit), and the time 610 taken to the sleep onset is changed from the increasing trend to a decreasing trend, and the ratio 710 occupied by the time of the REM sleep phase among the total sleep time is changed from the decreasing trend to the increasing trend, and the time 810 taken to the REM sleep stage is changed from the increasing trend to the decreasing trend, the specific time duration may be included in the follicular phases 531, 631, 731, and 831 among the biorhythm.

According to an embodiment, when the total sleep time 510 is changed from the decreasing trend to the increasing trend in the specific time duration, and the time 610 taken to the sleep onset is changed from the increasing trend to the decreasing trend, and the ratio 710 occupied by the time of the REM sleep phase among the total sleep time is in the decreasing trend, and the time 810 taken to the REM sleep phase is changed from the decreasing trend to the increasing trend, the specific time duration may be included in the ovulatory phases 532, 632, 732, and 832 among the biorhythm.

According to an embodiment, when the total sleep time 510 is in the increasing trend in the specific time duration, and the time 610 taken to the sleep onset is in the decreasing trend, and the ratio 710 occupied by the time of the REM sleep phase among the total sleep time is changed from the increasing trend to the decreasing trend, and the time 810 taken to the REM sleep phase is changed from the increasing trend to the decreasing trend, the specific time duration may be included in the luteal phases 533, 633, 733 and 833 among the biorhythm.

According to an embodiment, when the follicular phases 531, 631, 731, and 831, ovulatory phases 532, 632, 732, and 832 or luteal phases 533, 633, 733, and 833 of the biorhythm are determined, the order of the follicular phases 531, 631, 731, and 831, the ovulatory phases 532, 632, 732, and 832, and the luteal phases 533, 633, 733, and 833 may be considered for determination. For example, when a characteristic of at least one of the total sleep time 510, the time 610 taken to the sleep onset, the ratio 710 occupied by the time of the REM sleep phase among the total sleep time, or the time 810 taken to the REM sleep phase is different from a characteristic appearing in each of the follicular phases 531, 631, 731, and 831, the ovulatory phases 532, 632, 732, and 832, and the luteal phases 533, 633, 733, and 833, the biorhythm may be determined in consideration of the order of the follicular phases 531, 631, 731, and 831, the ovulatory phases 532, 632, 732, and 832, and the luteal phases 533, 633, 733, and 833. In an example, even if the ratio 710 occupied by the time of the REM sleep phase among the total sleep time is changed from the decreasing trend to the increasing trend in the specific time duration (e.g., a duration of a day unit), when a time duration in which this characteristic appears is between the ovulatory phase 732 and the luteal phase 733, the specific time duration may not be determined as the follicular phase 731 among the biorhythm.

Figure 9:
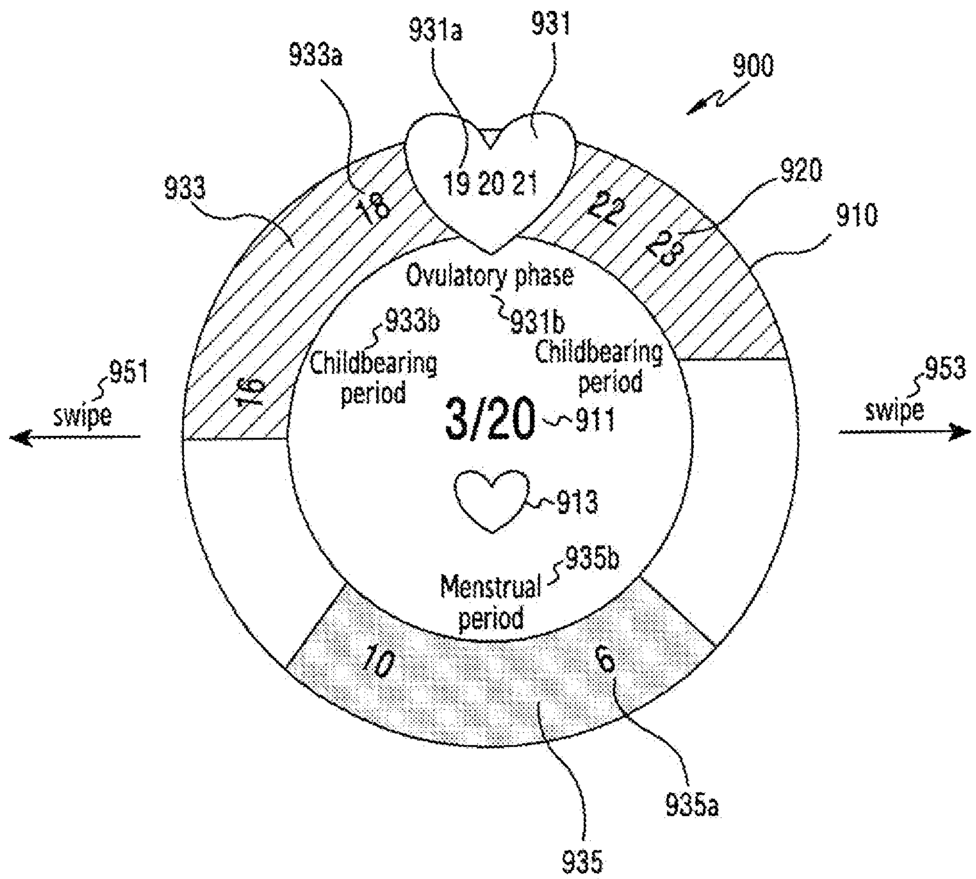
FIG. 9 is a diagram for explaining a user interface for presenting a biorhythm according to an embodiment of the present invention.
Figure 10:
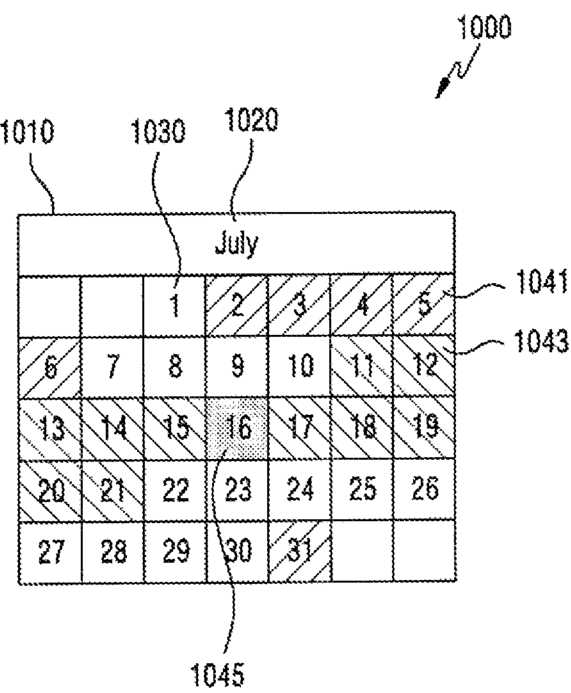
FIG. 10 is a diagram for explaining another user interface for presenting a biorhythm according to an embodiment of the present invention.

FIG. 9 is a diagram for explaining a user interface for presenting a biorhythm according to an embodiment of the present invention. FIG. 10 is a diagram for explaining another user interface for presenting a biorhythm according to an embodiment of the present invention.

Referring to FIG. 9 and FIG. 10, a processor (e.g., the processor 290 of FIG. 2) of an electronic device (e.g., the electronic device 200 of FIG. 2) may display information on a biorhythm on a display (e.g., the display 250 of FIG. 2). The processor may output a user interface (e.g., a first user interface 900 of FIG. 9 or a second user interface 1000 of FIG. 10) including the information on the biorhythm to the display.

The first user interface 900 may have a circular shape (e.g., a dial shape) as illustrated in FIG. 9. The first user interface 900 may include elements 920 of a specified time unit (e.g., a day unit) arranged at regular intervals on a circular time line 910. For example, in the first user interface 900, the element 920 corresponding to each of days included in a specific month may be arranged on the circular time line 910 at regular intervals.

The circular time line 910 may rotate wherein a current date is displayed at a specified location (e.g., an upper center). For example, the circular time line 910 may rotate clockwise (or counterclockwise).

According to an embodiment, a displayed month of the circular time line 910 may be changed according to a specified user gesture. For example, when a first gesture 951 (e.g., a swipe gesture to the left) is inputted on the first user interface 900, information corresponding to a previous month may be displayed based on a currently displayed month, and when a second gesture 953 (e.g., a swipe gesture to the right) is inputted on the first user interface 900, information corresponding to a next month may be displayed based on the currently displayed month.

The second user interface 1000 may have a rectangular shape (e.g., a calendar shape) as illustrated in FIG. 10. The second user interface 100 may include a square frame 1010 and elements 1030 of a specified time unit arranged on a grid formed inside the frame 1010. For example, in the second user interface 1000, a text 1020 indicating a specific month may be disposed in a specified area (e.g., an upper area) of the frame 1010, and the element 1030 corresponding to each of days included in the specific month may be arranged in the grid formed inside the frame 1010 except for the specified area.

The processor may set graphic characteristics of the elements 920 and 1030 according to a biorhythm including a time corresponding to the elements 920 and 1030. The graphic characteristics of the elements 920 and 1030 may include, for example, at least one of a color, font or size of a text (or number) indicating a time corresponding to the elements 920 and 1030, and a shape or color of a border of the elements 920 and 1030, or a background color or background image of the elements 920 and 1030.

The processor may set the graphic characteristics of the elements 920 and 1030 differently depending on which one of a follicular phase, ovulatory phase, and luteal phase of a biorhythm the time corresponding to the elements 920 and 1030 is included in. In this regard, the processor may set the biorhythm including a childbearing period or a menstrual period as well. In an example, as shown in FIG. 9, the processor may differently set and display, on the display, at least one of a shape (e.g., a heart shape) and color of a border of a first element 931*a* corresponding to a date included in a first period 931 of the biorhythm, a shape (e.g., a ring shape) and color of a border of a second element 933*a* corresponding to a date included in a second period 933 of the biorhythm, and a shape (e.g., a ring shape) and color of a border of a third element 935*a* corresponding to a third period 935 of the biorhythm. Here, the first period 931, the second period 933, or the third period 935 may be any one of the follicular phase, ovulatory phase, and luteal phase of the biorhythm. Or, the first period 931, the second period 933, or the third period 935 may be a childbearing period or a menstrual period (or menstruation period) as well. In another example, as illustrated in FIG. 10, the processor may differently set and display, on the display, a background color of a fourth element 1041 corresponding to a date included in a fourth period of the biorhythm and a background color of a fifth element 1043 corresponding to a date included in a fifth period of the biorhythm. Here, the fourth period or the fifth period may be any one of the follicular phase, ovulatory phase, and luteal phase of the biorhythm. Or, the fourth period or the fifth period may be a childbearing period or a menstrual period (or menstruation period) as well.

The processor may display objects 931*b*, 933*b*, and 935*b* indicating the type (e.g., a follicular phase, an ovulatory phase, a luteal phase, a childbearing period, or a menstrual period) of a menstrual cycle corresponding to each period, on the display. For example, as shown in FIG. 9, the processor may display a first text object 931*b* indicating the type of menstrual cycle corresponding to the first period 931 adjacently to the first element 931*a* included in the first period 931, and may display a second text object 933*b* indicating the type of menstrual cycle corresponding to the second period 933 adjacently to the second element 933*a* included in the second period 933, and may display a third text object 935*b* indicating the type of menstrual cycle corresponding to the third period 935 adjacently to the third element 935*a* included in the third period 935.

The processor may display at least one of an object 911 indicating a current date and an object 913 indicating the type of menstrual cycle corresponding to the current date, on the display. For example, as shown in FIG. 9, the processor may display a text object 911 indicating the current date and an image object 913 (e.g., a heart-shaped image) indicating the type of menstrual cycle corresponding to the current date, at the center of the first user interface 900 having a circular shape.

The processor may highlight and display an element 1045 corresponding to a user's interest cycle among a biorhythm. For example, the processor may set a graphic characteristic of the element 1045 corresponding to the interest cycle among the biorhythm to be different from graphic characteristics of the other elements 1041 and 1043. The interest cycle may include, for example, a day of ovulation or a day of menstruation. In an example, as shown in FIG. 10, the processor may set a background color of a sixth element 1045 corresponding to a specified date among the fifth period to be different from a background color of another element (e.g., the fourth element 1041 or the fifth element 1043), and display on the display.

The processor may display, on the display, a user interface capable of inputting at least one of user's activity information associated with a selected date and information on a health state, in response to selection of an element (e.g., the first element 931*a*, the second element 933*a*, the third element 935*a*, the fourth element 1041, the fifth element 1043, or the sixth element 1045) corresponding to a specific date included in a user interface (e.g., the first user interface 900 or the second user interface 1000). The user's activity information may include, for example, at least one of information on drinking before sleep, caffeine intake, food intake, and exercise performance. Also, the information on the user's health state may include, for example, at least one of information on menstrual volume, menstrual pain, back pain, acne, chest swelling, appetite, constipation, diarrhea, headache, blood pressure, dizziness, sweat, premenstrual syndrome, nausea, cervical mucus, itchiness, insomnia, tiredness, body aches, mood, BMI (weight/height), smoking, pregnancy test/ovulation test results, sex date, or whether or not to take hormonal/contraceptive pills.

Figure 11:
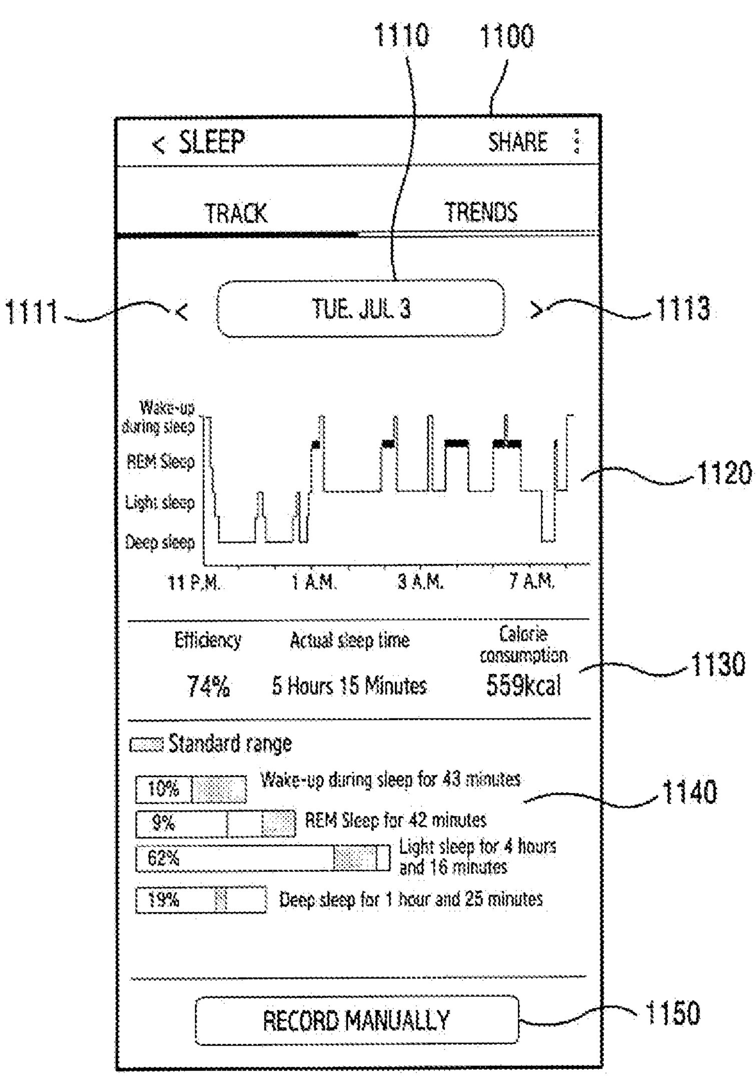
FIG. 11 is a diagram for explaining a user interface for presenting sleep information according to an embodiment of the present invention.
Figure 12:
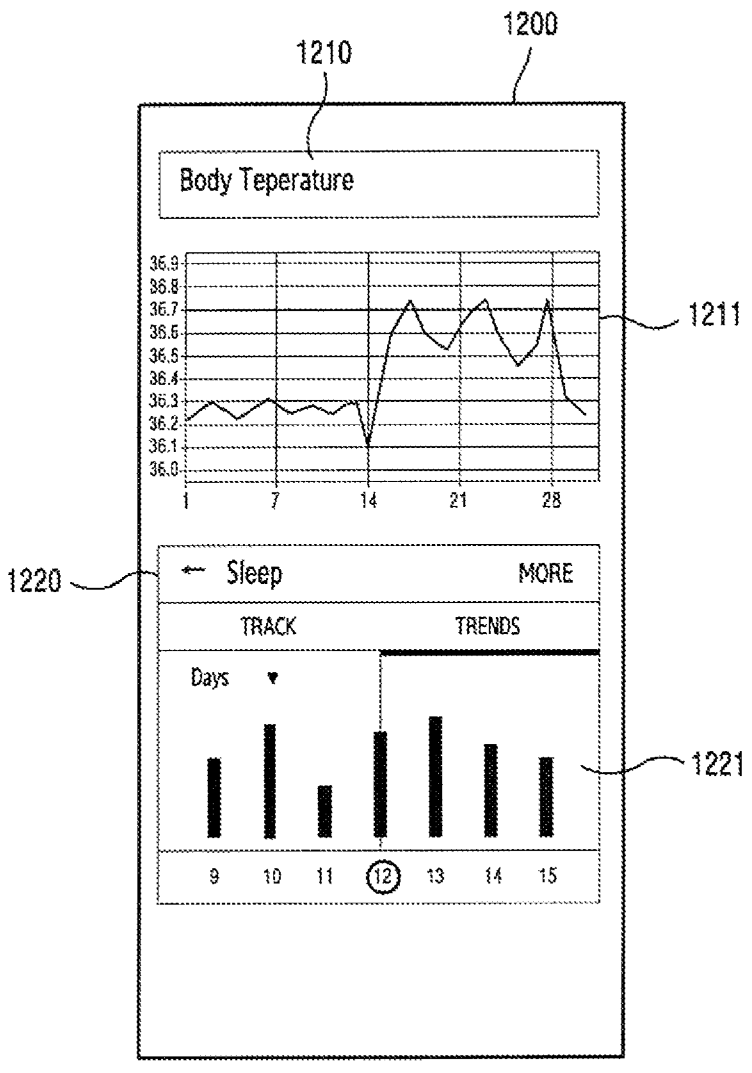
FIG. 12 is a diagram for explaining another user interface for presenting sleep information according to an embodiment of the present invention.

FIG. 11 is a diagram for explaining a user interface for presenting sleep information according to an embodiment of the present invention. FIG. 12 is a diagram for explaining another user interface for presenting sleep information according to an embodiment of the present invention.

Referring to FIG. 11 and FIG. 12, a processor (e.g., the processor 290 of FIG. 2) of an electronic device (e.g., the electronic device 200 of FIG. 2) may display sleep information on a display (e.g., the display 250 of FIG. 2). The processor may output a user interface (e.g., a third user interface 1100 of FIG. 11 or a fourth user interface 1200 of FIG. 12) including the sleep information to the display.

The user interfaces 1100 and 1200 including the sleep information may be displayed on the display, in response to selection of elements (e.g., the first element 931*a* of FIG. 9, the second element 933*a* of FIG. 9, the third element 935*a* of FIG. 9, the fourth element 1041 of FIG. 10, the fifth element 1043 of FIG. 10, or the sixth element 1045 of FIG. 10) corresponding to a specific date included in a user interface (e.g., the first user interface 900 of FIG. 9 or the second user interface 1000 of FIG. 10) including information on a biorhythm. For example, when the first element 931*a*, second element 933*a* or third element 935*a* included in the first user interface 900, or the fourth element 1041, fifth element 1043 or sixth element 1045 included in the second user interface 1000 is selected by a user input, the user interfaces 1100 and 1200 including sleep information related to a date corresponding to the selected element may be displayed on the display.

According to an embodiment, as shown in FIG. 11, the third user interface 1100 may include a currently selected date 1110, a button 1111 for selecting a previous date, a button 1113 for selecting a next date, a graph 1120 indicating a sleep stage dependent on time, an evaluation on sleep 1130 (e.g., a sleep efficiency, an actual sleep time, or a calorie consumption amount during sleep), a graph 1140 indicating a degree in which each sleep stage occupies in total sleep), and an editing button 1150.

According to an embodiment, as shown in FIG. 12, the fourth user interface 1200 may include a category 1210 presenting a user's body temperature, a graph 1211 indicating a change of a user's body temperature dependent on time, a category 1220 presenting sleep information, and a graph 1221 indicating a sleep state dependent on time.

The third user interface 1100 may include sleep information in a time duration of a day unit, and the fourth user interface 1200 may include sleep information in a time duration of a week unit or a month unit.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance.

According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with certain embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, The module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities, and some of the multiple entities may be separately disposed in different components. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

What is claimed is:

1. An electronic device comprising:

a circular housing:

a sensor module comprising a biometric sensor, a motion sensor and an environmental sensor;

a circular display corresponding to the circular housing;

at least one processor; and memory stores instructions that, when executed by the at least one processor, cause the electronic device to perform a plurality of operations comprising:

acquiring first sleep information related to an amount of a user's sleep through the sensor module, acquiring second sleep information related to a quality of the user's sleep through the sensor module, wherein the second sleep information comprises:

information, acquired through the biometric sensor, indicating a sleep disorder, environmental information, acquired through the environmental sensor, affecting the sleep, and information, acquired through the biometric sensor or the motion sensor, on the user's activity before the sleep, determining a biorhythm of the user, based on the first sleep information related to the amount of the sleep, determining whether a temporary sleep disorder occurs based on the environmental information affecting the sleep, and the information on the user's activity before the sleep, in case that the temporary sleep disorder occurs, maintain the biorhythm of the user, and in case that a non-temporary sleep disorder occurs, adjust the biorhythm of the user based on the information indicating the sleep disorder, display, via the circular display, a user interface for the biorhythm or the adjusted biorhythm, wherein the user interface comprises a circular dial with segments associated with dates, and the segments associated with dates are colored according to their respective phases of the biorhythm or adjusted biorhythm, and wherein the circular dial of the user interface corresponds to the circular display and circular housing.

2. The electronic device of claim 1, wherein the first sleep information and the second sleep information are acquired based on sensed information of the sensor module, and wherein the sensed information comprises at least one of information related to a movement of the electronic device, information related to a pressure applied from the outside of the electronic device, a user's respiration rate, heart rate, blood pressure, blood glucose, blood volume and/or oxygen saturation, information related to a sound provided by a user, or information related to a brightness of an external environment of the electronic device.

3. The electronic device of claim 1, wherein the first sleep information related to the amount of the user's sleep comprises at least one of an amount of time taken to sleep onset, a time taken to a REM sleep stage, a time of each sleep stage, a total sleep time, or a ratio of the time of each sleep stage to the total sleep time.

4. The electronic device of claim 3, wherein the plurality of operations further comprises determining a time duration of each sleep stage, based on the first sleep information.

5. The electronic device of claim 4, wherein the plurality of operations further comprises adjusting the determined time duration of each sleep stage, based on the second sleep information.

6. The electronic device of claim 1, wherein the plurality of operations further comprises:

determining an amount of change of the biorhythm, based on the determined biorhythm for a specified period, and when the amount of change of the biorhythm is greater than or equal to a specified magnitude, display notification information on the amount of change on the display.

7. The electronic device of claim 1, wherein the plurality of operations further comprises storing at least one of sensed information, the first sleep information, the second sleep information and information on the biorhythm in a secure area, or a secure hardware physically separated from the at least processor.

8. The electronic device of claim 1, wherein the first sleep information comprises an indication of low motion by a motion sensor for a continuous period of approximately eight hours.

9. The electronic device of claim 1, wherein the wherein the sensor module comprises photoplethysmography (PPG) sensor, wherein the first sleep information comprises an indication of a lower pulse rate.

10. A method comprising:

acquiring first sleep information related to an amount of a user's sleep through a sensor module comprising a biometric sensor, a motion sensor and an environmental sensor, acquiring second sleep information related to a quality of the user's sleep through the sensor module, wherein the second sleep information comprises:

information, acquired through the biometric sensor, indicating a sleep disorder, environmental information, acquired through the environmental sensor, affecting the sleep, and information, acquired through the biometric sensor or the motion sensor, on the user's activity before the sleep, determining a biorhythm of the user, based on the first sleep information related to the amount of the sleep, determining whether a temporary sleep disorder occurs based on the environmental information affecting the sleep, and the information on the user's activity before the sleep, in case that the temporary sleep disorder occurs, maintain the biorhythm of the user, and in case that a non-temporary sleep disorder occurs, adjust the biorhythm of the user based on the information indicating the sleep disorder, and display, via a circular display of an electronic device that corresponds to a circular housing of the electronic device, a user interface for the biorhythm or the adjusted biorhythm, wherein the user interface comprises a circular dial corresponding to the circular housing and the circular display, with segments associated with dates, and the segments associated with dates are colored according to their respective phases of the biorhythm or adjusted biorhythm.

11. The method of claim 10, wherein the first sleep information and the second sleep information are acquired based on sensed information of the sensor module, and wherein the sensed information comprises at least one of information related to a movement of the electronic device, information related to a pressure applied from the outside of the electronic device, a user's respiration rate, heart rate, blood pressure, blood glucose, blood volume and/or oxygen saturation, information related to a sound provided by a user, or information related to a brightness of an external environment of the electronic device.

12. The method of claim 10, wherein the first sleep information related to the amount of the user's sleep comprises at least one of an amount of time taken to sleep onset, a time taken to a REM sleep stage, a time of each sleep stage, a total sleep time, or a ratio of the time of each sleep stage to the total sleep time.

13. The method of claim 12, wherein determining the biorhythm comprises determining a time duration of each sleep stage, based on the first sleep information.

14. The method of claim 13, wherein determining the biorhythm further comprises adjusting the determined time duration of each sleep stage, based on the second sleep information.

15. The method of claim 10, further comprising:

determining an amount of change of the biorhythm, based on the determined biorhythm for a specified period, and when the amount of change of the biorhythm is greater than or equal to a specified magnitude, display notification information on the amount of change on the display.

16. The method of claim 10, further comprising storing at least one of sensed information, the first sleep information, the second sleep information and information the biorhythm in a secure area, or a secure hardware physically separated from at least one processor.

* * * * *